US008470978B2

(12) United States Patent
Gregory

(10) Patent No.: US 8,470,978 B2
(45) Date of Patent: Jun. 25, 2013

(54) METHOD FOR SEPARATING VIABLE CELLS, APOPTOTIC AND DEAD CELLS

(75) Inventor: Christopher Gregory, Edinburgh (GB)

(73) Assignee: Grampian Biopartners Limited, Aberdeen (GB)

(*) Notice: Subject to any disclaimer, the term of this patent is extended or adjusted under 35 U.S.C. 154(b) by 314 days.

(21) Appl. No.: 12/746,269

(22) PCT Filed: Dec. 5, 2008

(86) PCT No.: PCT/GB2008/004007
§ 371 (c)(1),
(2), (4) Date: Jul. 23, 2010

(87) PCT Pub. No.: WO2009/071892
PCT Pub. Date: Jun. 11, 2009

(65) Prior Publication Data
US 2010/0285034 A1 Nov. 11, 2010

(30) Foreign Application Priority Data

Dec. 5, 2007 (GB) .................................. 0723797.7

(51) Int. Cl.
C07K 16/00 (2006.01)
G01N 33/53 (2006.01)
A61K 39/395 (2006.01)

(52) U.S. Cl.
USPC ...... 530/388.1; 435/7.1; 435/810; 424/152.1; 424/141.1

(58) Field of Classification Search
None
See application file for complete search history.

(56) References Cited

U.S. PATENT DOCUMENTS

| 3,773,919 | A | 11/1973 | Boswell et al. |
| 4,816,567 | A | 3/1989 | Cabilly et al. |
| 5,215,927 | A | 6/1993 | Berenson et al. |
| 5,225,353 | A | 7/1993 | Berenson et al. |
| 5,641,870 | A | 6/1997 | Rinderknecht et al. |

FOREIGN PATENT DOCUMENTS

| EP | 0404097 | 12/1990 |
| WO | 93/11161 | 6/1993 |
| WO | 2006/079120 | 7/2006 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merckmanuals.com/professional/sec18/ch253/ch253e.html>. Breast Cancer. see pp. 1-8.*
Barbas, et al., "In vitro evolution of a neutralizing human antibody to human immunodeficiency virus type 1 to enhance affinity and broaden strain cross-reactivity", 1991, PNAS, 3809-3813.
Clackson, et al., "Making antibody fragments using phage display libraries", 1991, Nature, 352:624-628.
Dive, et al., "Analysis and discrimination of necrosis and apoptosis (programmed cell death) by multiparameter flow cytometry", Biochim Biophys Acta, 1992, 1133(3):275-285.
Gram, et al. "In vitro selection and affinity maturation of antibodies from a naive combinatorial immunoglobulin library", 1992, PNAS, 89:3576-3580.
Holliger, et al., "Diabodies: small bivalent and bispecific antibody fragments", 1993, Proc Natl. Acad. Sci. USA, 90:6444-6448.
Kabat, et al., 1991, Sequences of Proteins of Immunological Interest, US Dept. of Health and Human Services, Publish Health Service, Nat'l Inst. Of Health, NIH Publication No. 91/3242 and online at www.kabatdatabase.com http://immuno.bme.nwu.edu (Table of Contents).
Knappik, et al., "Fully synthetic human combinatorial antibody libraries (HuCAL) based on modular consensus frameworks and CDRs randomized with trinucleotides", 2000, J. Mol. Biol. 296, 57-86.
Kohler, et al., "Continuous cultures of fused cells secreting antibody of predefined specificity", 1975, Nature, 256:495-499.
Krebs, et al., "High-throughput generation and engineering of recombinant human antibodies", 2001, J. Immunol. Meth., 2154:67-84.
Marks, et al., "By-passing immunization: building high affinity human antibodies by chain shuffling", 1992, Bio/Technology, 10:779-783.
Morrison, et al., "Chimeric human antibody molecules: mouse antigen-binding domains with human constant region domains", 1984, Proc. Natl. Acad. Sci. USA, 81:6851-6855.
Ogden, et al., "Enhanced apoptotic cell clearance capacity and B cell survival factor production by IL-10-activated macrophages: implications for Burkitt's lymphoma", 2005, J. Immunol., 174, 3015.
Pluckthun, "Antibodies from *Escherichia coli*", 1994, The Pharmacology of Monoclonal Antibodies, vol. 113, Rosenburg and Moore eds., Springer-Verlag, New York, pp. 269-315.
Scier, "Isolation of picomolar affinity anti-c-erbB-2 single-chain Fv by molecular evolution of the complementarity determining regions in the center of the antibody binding site", 1996, J. Mol. Biol., 263-551:567.
Zapata, et al., "Engineering linear F(ab')2 fragments for efficient production in *Escherichia coli* and enhanced antiproliferative activity", 1995, Protein Eng 8(10):1057-1062.
Mourdjeva, M., et al., Apoptosis 2005; 10: 209-217.
Grunweald, S., et al., Cell and Tissue Banking 2001; 2: 127-133.
Hyun-Seok, Kim, et al., Biotechnol Lett 2007; 29: 1659-1663.
Sandstrom, K., et al., J. Immunological Methods 2000; 240: 55-68.
Lahorte, C., et al., Eur J Nucl Med Mol imaging 2004; 31: 887-919.

* cited by examiner

*Primary Examiner* — Sharon Wen
(74) *Attorney, Agent, or Firm* — McDonnell Boehnen Hulbert & Berghoff LLP

(57) ABSTRACT

Described are methods of separating viable cells, apoptotic cells and dead cells and antibodies or use in such methods. The antibodies may also be used in treatment of inflammatory disease, cancer and in wound healing.

14 Claims, 14 Drawing Sheets

Figure 1  Differential labelling of PI-negative BL cells with IMAB6 and IMAB7 following induction of apoptosis by staurosporine
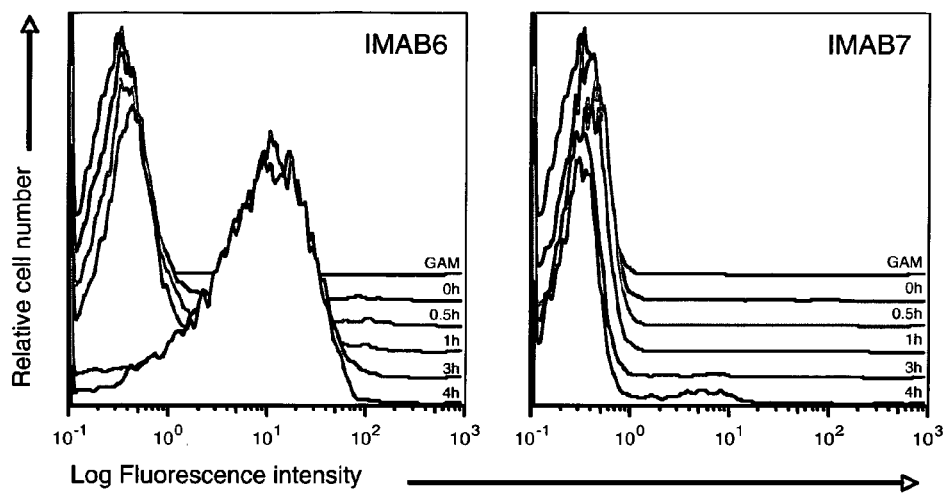
Figure 2  Identification of 'viable' and dead BL cells
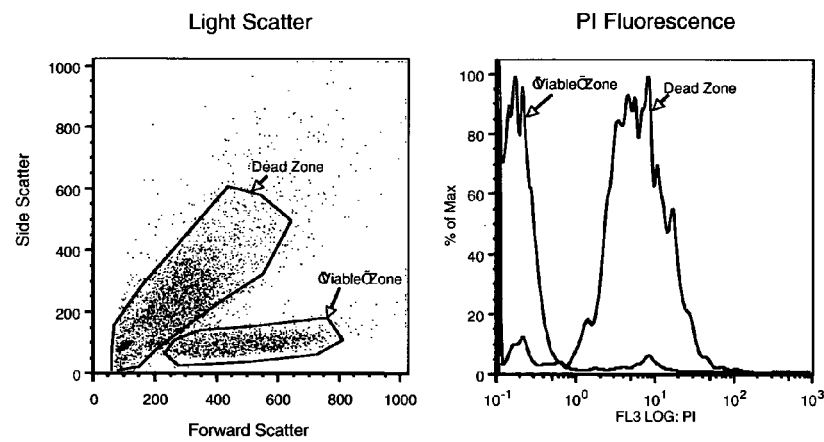

Figure 3  Differential labelling of PI-negative (apoptotic) and PI-positive (dead) BL cells with IMAB6 and IMAB7 following induction of apoptosis by staurosporine
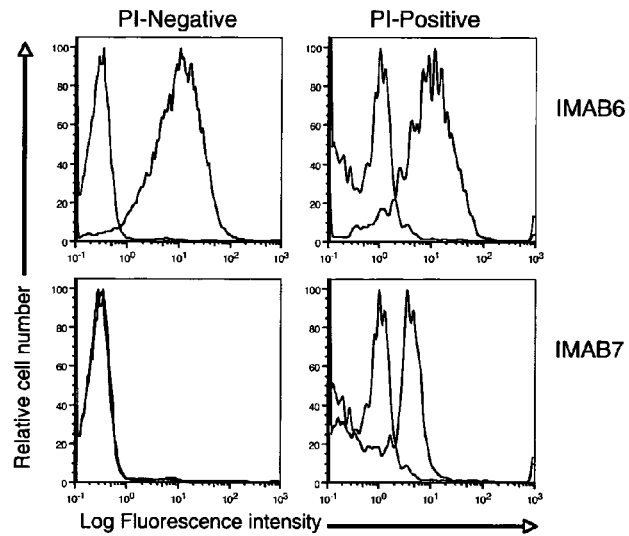
Figure 4  Differential labelling of BL cells in 'viable' and dead light-scatter zones with IMAB6 and IMAB7 following induction of apoptosis by staurosporine
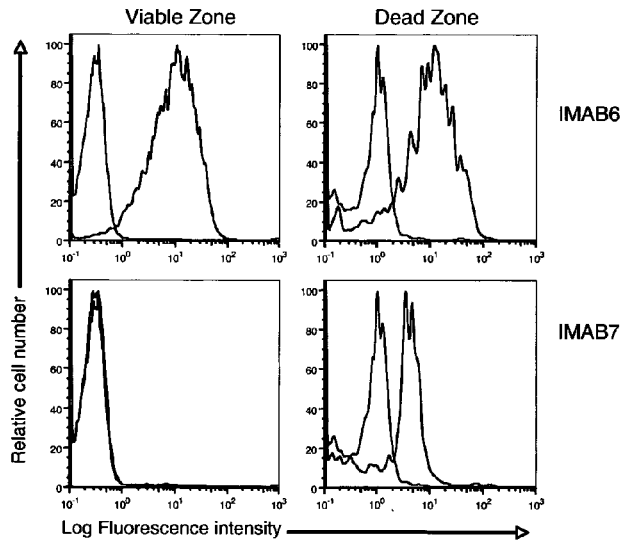

Figure 5   Gradual appearance of apoptotic cells in the 'viable' light scatter zone following induction of apoptosis in BL cells using staurosporine
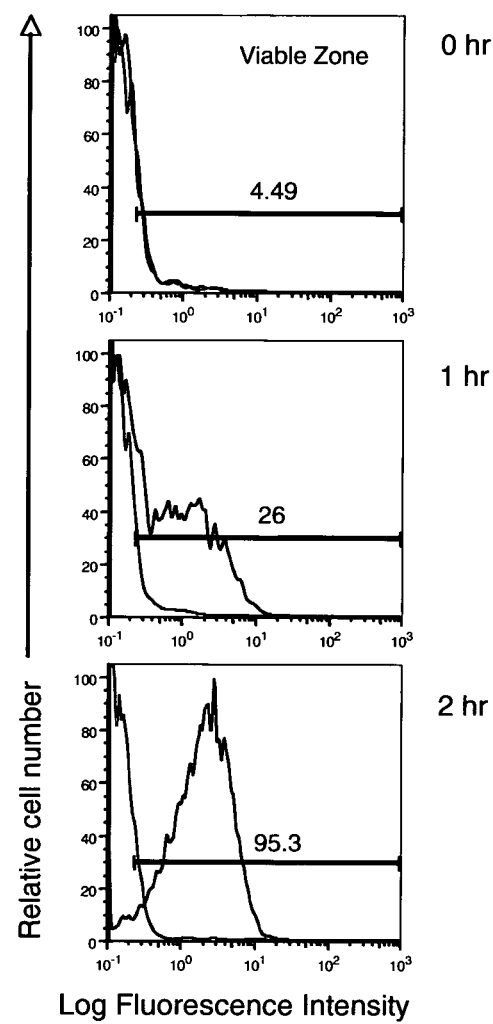

Figure 6 Gradual appearance of apoptotic cells in the 'viable' light scatter zone following induction of apoptosis in BL cells after frozen storage
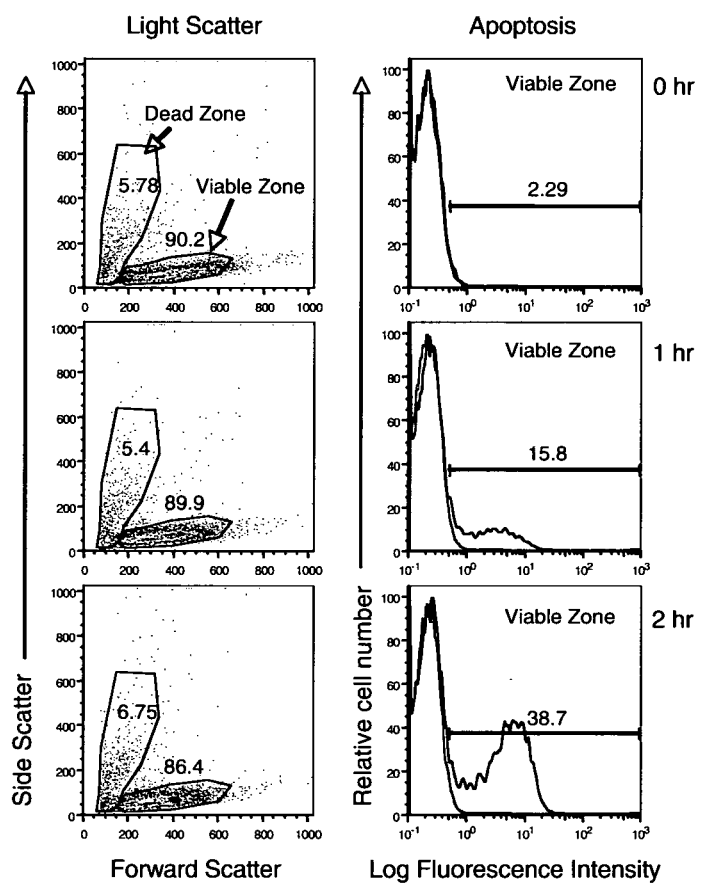

Figure 7    Comparable reactivates of annexin V and IMAB6 on apoptotic thymocytes
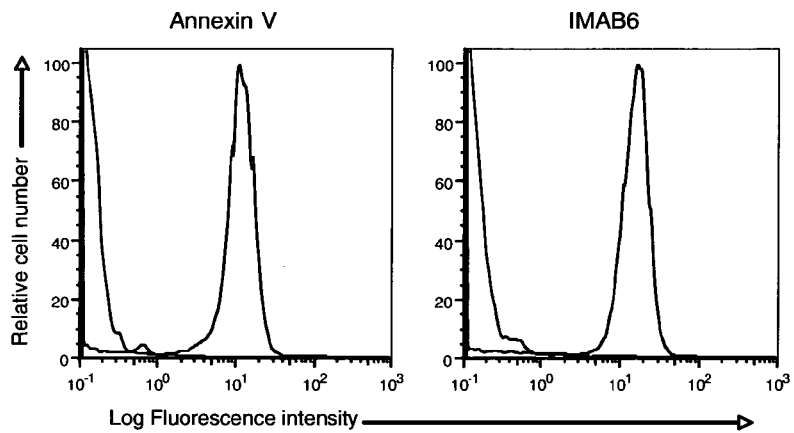
Figure 8    Comparable reactivates of annexin V and IMAB6 on PI-negative, apoptotic BL cells
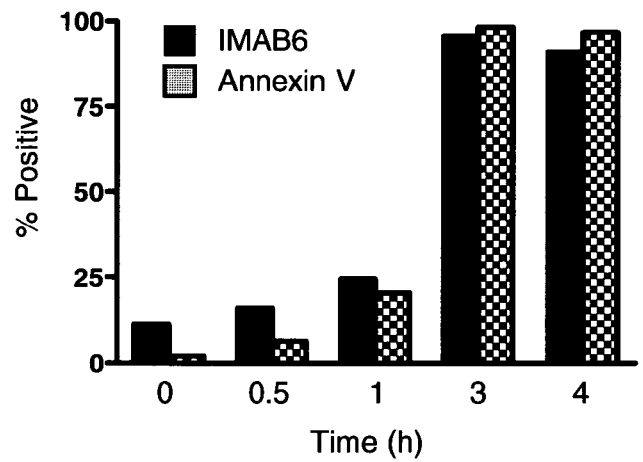

Figure 9    IMAB6 and IMAB7 react with phospholipids phosphatidylserine (PS) and phosphatidylglycerol (PG)
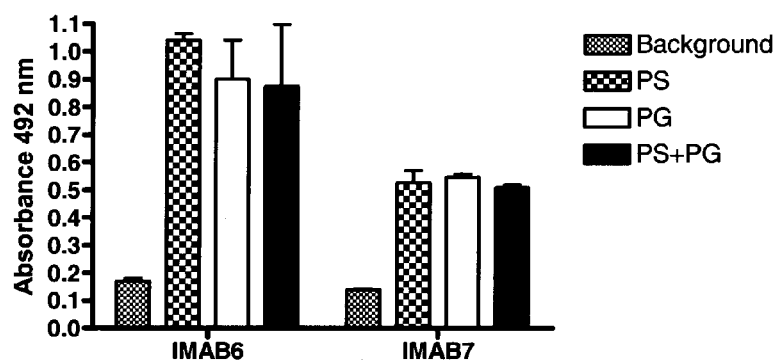
Figure 10    Direct depletion of dead cells by IMAB6-coupled magnetic particles
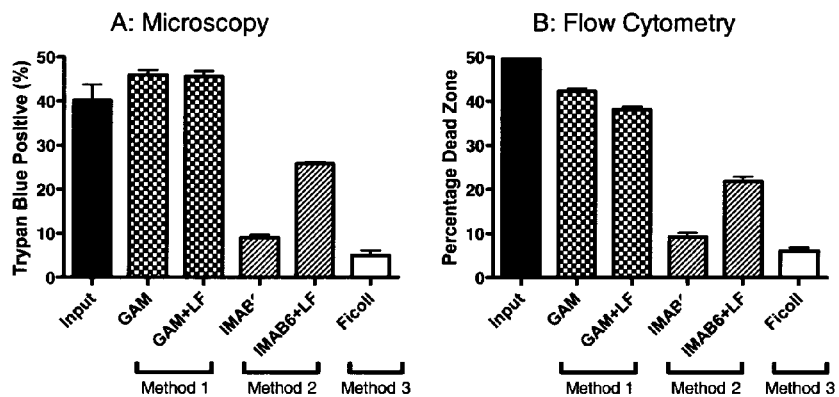

Figure 11  Interactions of cells with magnetic particles for dead-cell depletion are not improved by sample rotation
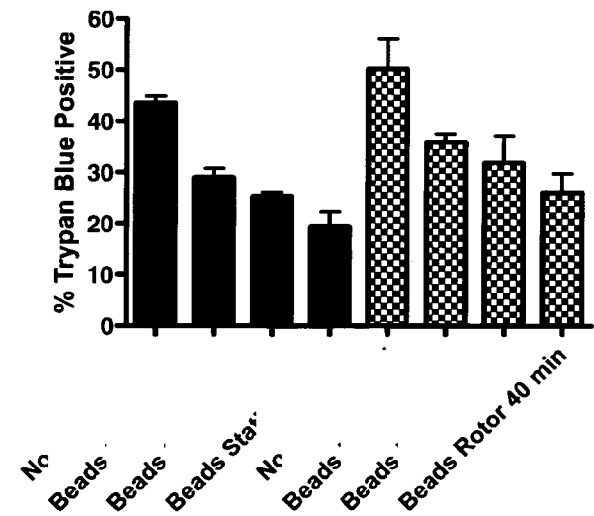
Figure 12  Efficient depletion of dead BL cells by IMA6-coupled magnetic particles in complete culture medium at 37°C
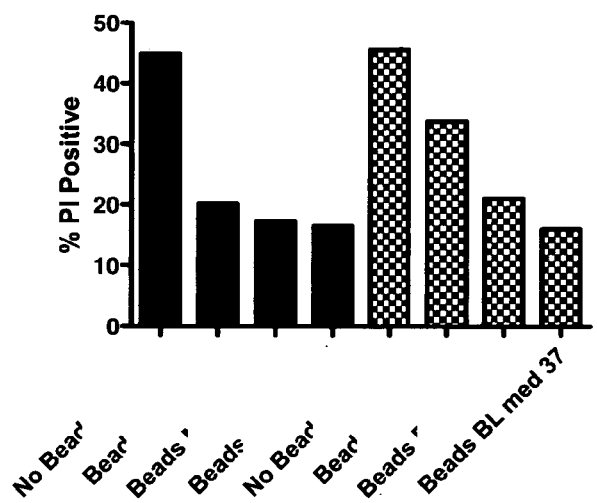

Figure 13    Depletion of dead BL cells by IMA6-coupled magnetic particles in complete culture medium at 37°C: effect of time of interaction
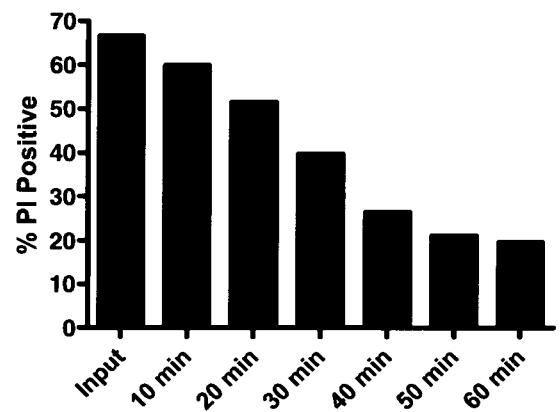
Figure 14    Direct dead-cell depletion from BL cultures by IMAB6-coupled 300 and 500 nm magnetic particles
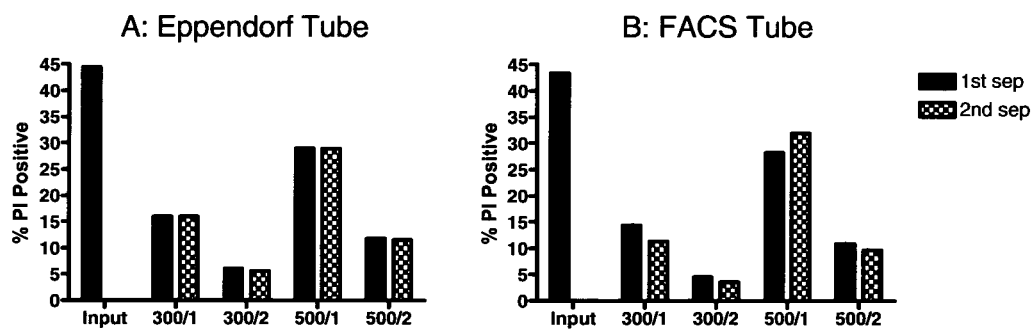

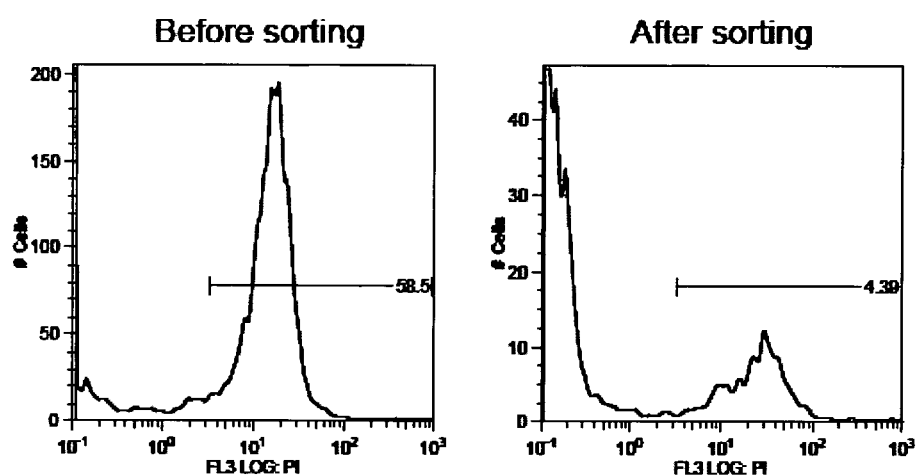
Figure 15 Use of IMAB-6 to separate viable and dead cells by flow cytometry Figure 16 Detection of microparticles released from apoptotic cells by IMAB-6 labelling
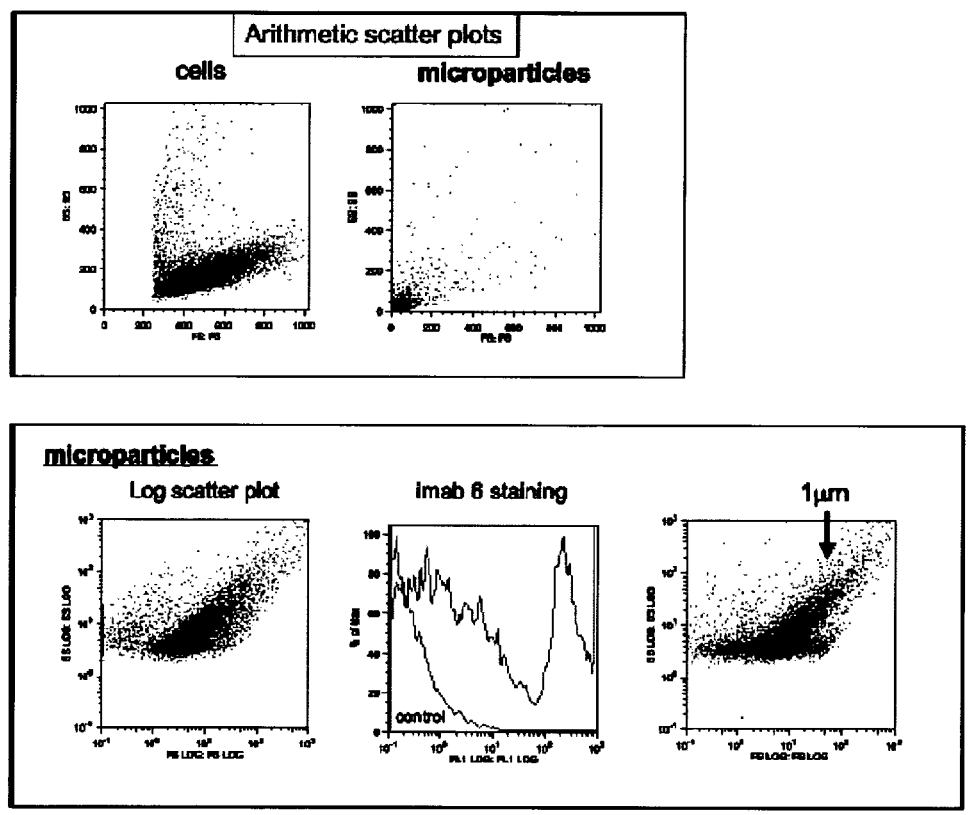

Figure 17 Separation of microparticles, blebs and apoptotic cells
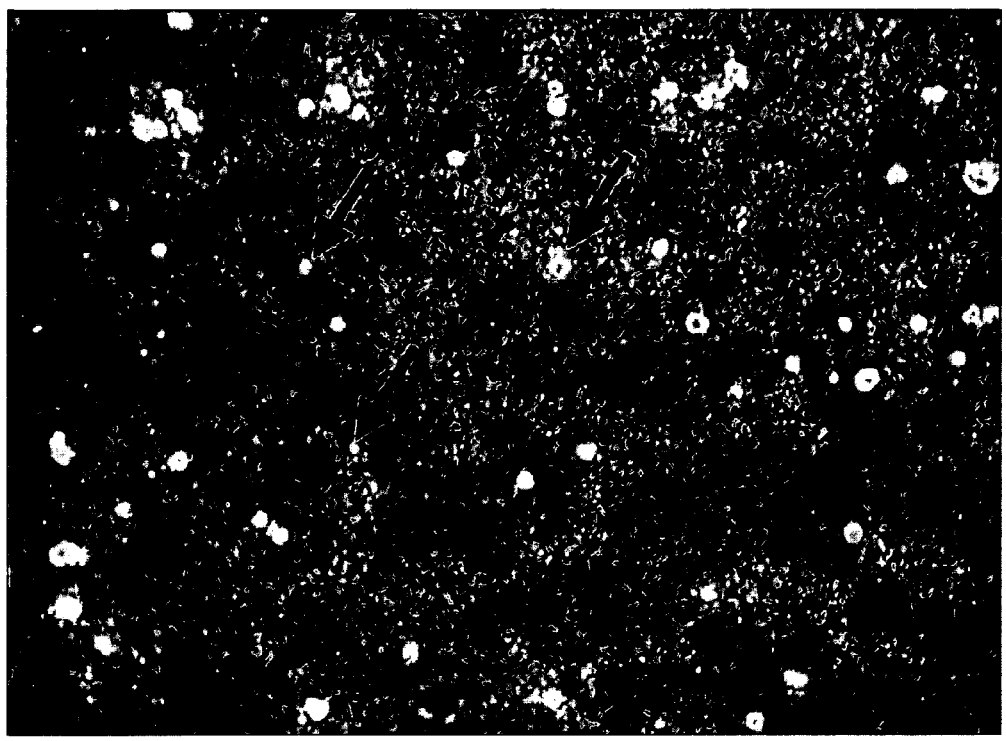

Figure 19

IMAB-6 Heavy Chain V-region

```
 51 CTGCAGGTGT CCACTCCCAG GTTCAGCTGC AGCAGTCTGG AGCTGAGCTG
                         Q   V   Q   L   Q   Q   S   G   A   E   L

101 ATGAAGCCTG GGGCCTCAGT GAAGATATCC TGCAAGGCTA CTGGCTACAC
     M   K   P   G   A   S   V   K   I   S   C   K   A   T   G   Y   T    CDR-H1

151 ATTCAGTAGC TACTGGATAG AGTGGGTAAA GCAGAGGCCT GGACATGGCC
     F   S   S   Y   W   I   E    W   V   K   Q   R   P   G   H   G   L

201 TTGAGTGGAT TGGAGAGATT TTACCTGGAA GTGGTAGTAC TAACTACAAT
     E   W   I   G   E   I   L   P   G   S   G   S   T   N   Y   N    CDR-H2

251 GAGAAGTTCA AGGGCAAGGC CACATTCACT GCAGATACAT CCTCCAACAC
     E   K   F   K   G   K   A   T   F   T   A   D   T   S   S   N   T

301 AGCCTACATG CAACTCAGCA GCCTGACATC TGAGGACTCT GCCGTCTATT
     A   Y   M   Q   L   S   S   L   T   S   E   D   S   A   V   Y   Y

351 ACTGTGCAAG AGGGGGGACA GCTCGGGCTA CCCACTATGC TATGGACTAC
     C   A   R   G   G   T   A   R   A   T   H   Y   A   M   D   Y    CDR-H3

401 TGGGGTCAAG GAACCTCAGT CACCGTCTCC TCAGAGAGTC ATCTGGCC    SEQ ID NO: 9
     W   G   Q   G   T   S   V   T   V   S   S                         SEQ ID NO: 10
```

Figure 20

IMAB 6 Kappa V-region and Constant region

```
 51 CCGCGGGAAT TCGATTTCTG GCGGTGGCGG ATCGGATATT GTGATAACCC
                                              D  I  V  I  T  Q

101 AGACTCCCAA ATTCCTGCTT GTATCAGCAG GAGACAGGGT TACCATAACC
     T  P  K  F  L  L  V  S  A  G  D  R  V  T  I  T

151 TGCAAGGCCA GTCAGAGTGT GAGTAATGAT GTAGCTTGGT ACCAACAGAA
     C  K  A  S  Q  S  V  S  N  D  V  A  W  Y  Q  Q  K       CDR-L1

201 GCCAGGGCAG TCTCCTAAAC TGCTGATATA CTATGCATCC AATCGCTACA
     P  G  Q  S  P  K  L  L  I  Y  Y  A  S  N  R  Y  T       CDR-L2

251 CTGGAGTCCC TGATCGCTTC ACTGGCAGTG GATATGGGAC GGATTTCACT
     G  V  P  D  R  F  T  G  S  G  Y  G  T  D  F  T

301 TTCACCATCA GCACTGTGCA GGCTGAAGAC CTGGCAGTTT ATTTCTGTCA
     F  T  I  S  T  V  Q  A  E  D  L  A  V  Y  F  C  Q       CDR-L3

351 GCAGGATTAT AGCTCTCCGT ACACGTTCGG AGGGGGGACC AAGCTGGAAA
     Q  D  Y  S  S  P  Y  T  F  G  G  G  T  K  L  E  I

401 TAAAACGGGC TGATGCTGCA CCAACTGTAT CCATCTTCCC ACCATCCAGT
     K  R  A  D  A  A  P  T  V  S  I  F  P  P  S  S          C-Region 451 GAGCAGTTAA CATCTGGAGG TGCCTCAGTC GTGTGCTTCT TGAACAACTT
     E  Q  L  T  S  G  G  A  S  V  V  C  F  L  N  N  F 501 CTACCCCAAA GACATCAATG TCAAGTGGAA GATTGATGGC AGTGAACGAC
     Y  P  K  D  I  N  V  K  W  K  I  D  G  S  E  R  Q 551 AAAATGGCGT CCTGAACAGT TGGACTGATC AGGACAGCAA AGACAGCACC
     N  G  V  L  N  S  W  T  D  Q  D  S  K  D  S  T 601 TACAGCATGA GCAGCACCCT CACGTTGACC AAGGACGAGT ATGAACGACA
     Y  S  M  S  S  T  L  T  L  T  K  D  E  Y  E  R  H 651 TAACAGCTAT ACCTGTGAGG CCACTCACAA GACATCAACT TCACCCATTG
     N  S  Y  T  C  E  A  T  H  K  T  S  T  S  P  I  V 701 TCAAGAGCTT CAACAGGAAT GAGTGTAATC ACTAGTGAAT TCGCGGCCGC   SEQ ID NO: 11
     K  S  F  N  R  N  E  C                                   SEQ ID NO: 12
```

METHOD FOR SEPARATING VIABLE CELLS, APOPTOTIC AND DEAD CELLS

PRIORITY

This application is a national stage entry of International Application No. PCT/GB2008/004007, filed on Dec. 5, 2008, which claims the benefit of the filing date of GB Application Ser. No. 0723797.7, filed Dec. 5, 2007. The entire contents of the foregoing applications are incorporated by reference herein in their entirety.

FIELD OF THE INVENTION

The present invention relates to methods for the detection of dead and dying cells, reagents for use in such methods and uses of such reagents.

BACKGROUND TO THE INVENTION

Apoptosis is a fundamentally important process in normal development and homeostasis. Apoptosis is also known to play a role in many disease states. For example, apoptosis and defects in apoptotic pathways are believed to be particularly relevant to cancer, heart disease, stroke, Alzheimer's disease, ischaemia and autoimmune diseases. For example, cancers may result from a defect in the apoptosis pathway, even in the absence of an increased proliferation rate.

Anti-cancer drug candidates failing to induce apoptosis are likely to have decreased clinical efficacy, making apoptosis assays important tools for high-throughput drug screening. The development of apoptosis modulating drugs requires robust assays for determining the presence of apoptotic and/or dead cells. Although a number of methods are available in the prior art to identify and/or quantify the presence of apoptotic and/or dead cells in a biological sample, for example a blood sample or a biopsy sample, the methods each suffer from specific disadvantages.

A number of methods are known in the art for assaying apoptosis. Nucleic acid stains may be used to identify apoptotic cells in cell populations, taking advantage of the characteristic breakdown of the nucleus during apoptosis, which results in collapse and fragmentation of the chromatin, degradation of the nuclear envelope and nuclear blebbing, resulting in the formation of "micronuclei".

Other methods used in the prior art include measurement of protease activity in cells, for example, measurement of the activity of effectors of the apoptosis pathway, such as caspase-3 and caspase-8. As a characteristic of apoptosis is the disruption of active mitochondria, mitochondrial stains may be used to identify apoptotic cells. Other apoptosis assays employ free radical probes or ion indicators to measure changes in apoptotic cells. One of the most commonly used assays of apoptosis is based on the use of the vascular anti-coagulant annexin V. Annexin V is a phospholipid-binding protein that has a high affinity for phosphatidylserine. However, in viable cells, annexin V does not bind phosphatidylserine as it is located on the cytoplasmic surface of the cell membrane. In apoptotic cells, however, phosphatidylserine is externalised to the outer surface of the plasma membrane, where it can be bound by annexin V. However, the use of annexin V in assays for the detection of apoptosis suffers from a number of disadvantages. In particular, as binding of annexin V to phosphatidylserine is $Ca^{2+}$ dependent, the choice of buffer used in assays is limited. This usually requires a change of buffer prior to a sample being assayed, which is not only time-consuming but can cause increased stress to cells and result in an increase in non-viable cells.

As well as being used in the detection methods, antibody based techniques are commonly used in separation techniques, such as in the separation of sub-populations of cells in particular samples. Magnetic particles are routinely used to fractionate cells within populations of viable cells of multiple lineages (commonly lymphocyte subsets, monocytes, dendritic cells, stem cells, tumour cells etc) from many different species (human, mouse, rat, non-human primates and others). Generally, to ensure high fractionation efficiency, selection of cell populations is through indirect means: typically one or more primary antibodies are allowed to bind to cells and the antibody-bound cells are pulled out using magnetic particles coupled to a secondary antibody or, if the primary antibodies are biotinylated, (strept)avidin. Moreover such techniques generally require to be performed, at least in part, at low non-physiological temperatures and/or in the presence of buffers that differ in composition from the culture medium that is most suitable to support the viability of the cells in question.

There is therefore a need for further assays which may be used for detecting the presence of non-viable cells in a sample, for example, for use in high throughput assays and simple separation techniques which overcome some of the problems of the prior art techniques, in particular for techniques which may be used with minimal perturbation of physiological conditions of cells, such as optimal culture conditions (since perturbation reduces viability).

SUMMARY OF THE INVENTION

The present inventors have identified a detectable reagent that is selectively bound to dead and dying cells, and that does not require non-physiological temperatures or high calcium concentration in order to selectively bind (as is required by currently known methods that employ, for example, Annexin V). Moreover, the inventors have developed a simple novel cell separation technique that can be used under substantial physiological conditions, such as those in which cells are typically maintained in culture. As shown in the Examples, the inventors, to their own surprise, have demonstrated that antibodies directed to epitopes on apoptotic or dead cell components may be used directly with high efficiency to separate such cell components or cells from other cells or cell components in a sample under physiological conditions.

Accordingly, in a first aspect of the present invention, there is provided a method of separating a target cell or cell component from a sample, said method comprising:

contacting said sample with an antibody molecule which specifically binds said target cell or cell component;

allowing said antibody molecule to form a conjugate with said target cell or cell component;

and separating said conjugate from said sample; wherein said separation step is performed under physiological conditions.

In one embodiment, the step of allowing the antibody molecule to form a conjugate with said target cell is performed under physiological conditions.

In the context of the present invention, "physiological conditions" refers to a temperature in the range 30-45° C., for example 35-41° C.

Many prior art separation techniques—for example those that utilise annexin V—require very specific conditions, for example high calcium concentrations, for example greater than 2.3 mM. It has been found that, contrary to such prior art separation techniques, the method of the invention may be performed over a wide range of calcium concentrations, including minimal or no free $Ca^{2+}$, a condition that minimises cell clumping, which is a fundamental problem in cell separation. In one embodiment of the invention, the term physiological further refers to a calcium concentration which is less than 2.3 mM, for example less than 2.0 mM, such as less than 1.5 mM, for example less than 1 mM. In one embodiment, the method is performed at physiologically normal levels of calcium, for example in the range 1.8 to 2.2 mM.

In another embodiment, the method is performed in the presence of a calcium chelator, such as EDTA, at a concentration which substantially chelates free $Ca^{2+}$, for example 2 mM.

Moreover, to the inventors' surprise, it has been found that such antibody based techniques for separating dead cell components or entire cells from a sample may be efficiently carried out without the need for a secondary binding moiety, e.g. a secondary antibody or secondary protein such as strept (avidin). In general, antibody-based cell separation techniques, which, to date, have been largely limited to separation of different sub-types of live cells or live cell components, have required the use of a secondary antibody. Typically, a target cell is bound by a primary antibody with subsequent separation steps involving capture with a secondary antibody or, in the case where the primary antibody is labelled, with, for example, biotin, capture with a capture moiety, for example (strept)avidin. As described in the examples, the present inventors have shown that, using the method of the first aspect of the present invention, dying, dead cells or components from dying or dead cells may be separated from a sample without the need to use either a secondary antibody or, indeed, primary antibodies labelled with, for example, biotin. The inventors have shown that primary antibodies bound directly to magnetic beads efficiently bind target dead cell components in a sample and, by application of a magnetic field, can be used to separate such cells or cell components from said sample. Indeed, as shown in the examples, with respect to the antibodies tested, to the inventors' great surprise, the efficiency of separation using such a "direct" technique was substantially equivalent, if not greater, than the efficiency of separation using a primary and secondary antibody system, as conventionally applied to live cell separation techniques.

Accordingly, in one embodiment of the present invention, the separation step does not involve the use of a secondary binding moiety.

In such embodiments, the antibody molecule for use in the invention is provided as a conjugate with a substrate which enables separation. Such substrate may be a magnetic particle or bead. In other embodiments, the substrate is a solid substrate, such as that used in column separation techniques, a polystyrene bead etc. The antibody may be coupled to such substrates using conventional methods.

In a particular embodiment of the invention, the antibody molecule is coupled to a magnetic particle, for example a magnetic bead.

Although some prior art systems e.g. Miltenyi, use very small beads (less then 100 nm) that allow efficient positive (though not efficient negative) selection of cell populations sometimes without the use of secondary antibody or streptavidin, such systems require high gradient magnetic fields (HGMF) to mediate magnetic separation. Typically, HGMFs for cell separation are generated using a column of steel wire (through which the cell suspension is passed) to which a powerful magnetic field in the range 0.6-1 Tesla is applied.

The inventors have surprisingly shown that, in distinct contrast to such systems, the present invention may be used to achieve high-efficiency separation of viable cells by direct negative selection. Moreover, it may be used to attain high-efficiency negative selection using beads which are sufficiently highly super-paramagnetic to be separable by a simple magnet, ie without the need for a HGMF.

Accordingly, in one embodiment of the invention, the separation step is performed using a conventional magnetic field i.e. in the absence of a high gradient magnetic field. The conventional magnetic field may be generated using any conventional magnet; examples of magnets which may be used include the EasySep magnet from StemCell technologies (Cat No. 18000), and (2) the Adem-Mag SV magnet from Ademtech (Cat No. 20101).

In one embodiment, the method is performed using a magnetic bead or particle of diameter greater than 125 nm, such as greater than 150 nm, for example, greater than 250 nm. However, smaller magnetic beads or particles which can be separated using conventional magnets may also be used. For example, superparamagnetic beads of approximately 40 nm size are known in the art and may be used in one or more embodiments of the present invention.

The antibody molecule for use in the present invention may be of any immunoglobulin class, for example IgM, IgE, IgA or IgG. In one particular embodiment of the invention, the antibody molecule is an IgM antibody.

The present inventors have found that IgM antibodies show particular efficiency in the separation of a sub-population of cells or cell components from a mixed population without the need for a secondary binding moiety, for example secondary antibody. The surprisingly efficient separation observed using such IgM antibody molecules enables their use in the separation of live cells or components thereof from a population of cells, as well as the separation of non-viable cells or components thereof, from a mixed population of viable and non-viable cells, or components thereof.

Accordingly, in a second, independent aspect of the present invention, there is provided a method of separating a target cell or cell component from a sample, said method comprising:

contacting said sample with an IgM antibody molecule which specifically binds said target cell or cell component;

allowing said IgM antibody molecule to form a conjugate with said target cell;

and separating said conjugate from said sample; wherein said separation does not involve the use of a secondary binding moiety.

In one embodiment, said method is performed under physiological conditions of temperature and or calcium concentration.

The inventors have shown that antibody molecules directly conjugated to magnetic beads may be used to bind a target antigen in a sample, and, by the application of a magnetic field, be used to separate such target cells or cell components on which the antigen is present from other sample components.

In one embodiment of the first or second aspect of the invention, the antibody molecules are molecules with binding specificity for cells or cell components of non-viable cells, for example dead or apoptotic cells. In such embodiments, the method of the invention may be used in the removal of such cells from a population of cells. Thus, in one embodiment of the invention, the target cell is a non-viable cell and said method is a method of separating non-viable cells or their components from viable cells.

As described in the Examples, the inventors have developed a novel antibody with binding specificity for an epitope on cells which are apoptotic or dead. The hybridoma cell line that produces the antibody, herein referred to as IMAB6, has been deposited with European Collection of Cell Cultures (ECACC), Heath Protection Agency, Centre for Emergency Peparedness and Response, Porton Down, Salisbury, Wiltshire, SP4 0JG, United Kimgdom, on 4 Dec. 2007 under provisional accession no: 07120409.

The inventors have further developed a novel antibody with binding specificity for an epitope, which is exposed on cells which are dead but is not exposed on intact cells, including apoptotic intact cells. The hybridoma cell line that produces the antibody, herein referred to as IMAB7, has been deposited with ECACC on 4 Dec. 2007 under provisional accession no: 07120410.

Without being limited to any one theory, it is believed that both IMAB6 and IMAB7 have binding specificity for a different epitope of phosphatidylserine, the epitope to which IMAB6 binds being present on a portion of phosphatidylserine which is presented extracellularly only when a cell is apoptotic or lysed, and the epitope to which IMAB7 binds being present on a portion of phosphatidylserine which is intracellular and thus exposed only after lysis.

In one embodiment of the methods of the invention, the antibody molecule is IMAB6. In another embodiment, the antibody molecule is IMAB7. Indeed, such antibodies represent third and fourth independent aspects of the present invention.

The provision of the antibodies of the present invention enables the development of related antibodies and antibody molecules which also selectively bind to dead and dying cells.

Thus, encompassed by the third aspect of the present invention is an antibody molecule with binding specificity for dead and apoptotic cells wherein said antibody molecule comprises one or more of CDRL1, CDRL2, CDRL3, CDRH1, CDRH2 and CDRH3 of the IMAB 6 antibody molecule obtainable from the cell line deposited with ECACC under accession no: 07120409. In a particular embodiment of the invention, said antibody molecule comprises (i) CDRL1, CDRL2, and CDRL3, and/or (ii) CDRH1, CDRH2 and CDRH3 of the IMAB6 antibody molecule obtainable from the cell line deposited with ECACC under accession no: 07120409.

Encompassed by the fourth aspect of the present invention is an antibody molecule with binding specificity for dead and apoptotic cells wherein said antibody molecule comprises one or more of CDRL1, CDRL2, CDRL3, CDRH1, CDRH2 and CDRH3 of the IMAB 7 antibody molecule obtainable from the cell line deposited with ECACC under accession no: 07120410. In a particular embodiment of the invention, said antibody molecule comprises (i) CDRL1, CDRL2, and CDRL3, and/or (ii) CDRH1, CDRH2 and CDRH3 of the IMAB7 antibody molecule obtainable from the cell line deposited with ECACC under accession no: 07120410.

In one embodiment of this aspect of the invention, the antibody molecule is an IgM molecule. However, the antibody may be of any class and so may be IgG, IgE, IgA or IgM.

The antibodies of the invention may be used in any method of separating an apoptotic cell, dead cell or dead cell component from a sample.

Accordingly, in a fifth aspect of the invention, there is provided a method of separating a target cell or cell component from a sample, said method comprising:

contacting said sample with an antibody molecule of the third or fourth aspect of the invention;

allowing said antibody molecule to form a conjugate with said target cell or cell component;

and separating said conjugate from said sample, wherein said target cell or cell component is a non-viable cell or component.

The methods and antibodies of the invention, by enabling the separation of dead cells from viable cells, find particular utility in the enrichment of populations of cells to ensure maximum numbers of live cells, for example in cell culture. The ability of the antibodies to be used in substantially physiological conditions, in particular at physiological temperature, finds particular utility in the enrichment of cells in culture. Without the disadvantage of perturbing normal physiological conditions to remove dead cells, cells in cell culture may be maintained under optimal conditions.

Accordingly, in a sixth aspect of the invention there is provided a method of enriching a population of cells in a sample, said method comprising removal of a target cell from said sample using the method according to the first, second, or fifth aspect of the present invention.

As well as finding utility in the separation of cells, the antibodies of the invention may also be used in simple detection techniques. As described above, IMAB6 has been found to have specificity for non-viable cells, binding both dead cells and apoptotic cells, whereas IMAB7 has binding selectivity for dead cells only.

Thus, a seventh aspect of the present invention provides a method of detecting non-viable cells or cell components thereof in a sample, the method comprising the steps of:

contacting the sample with an antibody molecule according to the third or fourth aspects of the present invention, and detecting binding of the antibody molecule to said cells or cell components.

Where it is necessary to identify both dead and apoptotic cells, antibodies of the third aspect of the invention may be used. In many situations, there will be no need to distinguish between different types of non-viable cells, for example, dead and apoptotic cells.

However, in some embodiments, it may be useful to distinguish between such cells. Thus, in one preferred embodiment of the seventh aspect of the invention, the method further comprises the step of distinguishing cells that have undergone lysis from intact cells.

Any suitable method of distinguishing cells that have undergone lysis from intact cells known in the art may be used. For example, detectable markers of lysed cells may be used. In one embodiment, the detectable marker is propidium iodide. Other detectable markers which may be used include cell impermeant ethidium agents eg. ethidium homodimer-1; 7-aminoactinomycin D: TO-PRO-3 iodide (all available from Molecular Probes).

Alternatively, or in addition, the detectable marker may comprise an antibody molecule capable of binding to lysed cells.

In a particular embodiment of the invention, where it is desired to detect dead cells only, antibody molecules according to the fourth aspect of the invention may be used.

A particular advantage of antibodies IMAB6 and IMAB7 is that each is sufficiently robust to survive fixation following binding. Typically in the study of apoptosis standard staining techniques, such as antibody based techniques, typically a combination of annexin V and propidium iodide, are not amenable to fixation, thereby requiring immediate analysis of samples after labelling. However, in contrast, the IMAB6 and the IMAB7 antibodies are robust, their bonds with cells and cell components to which they are attached not being broken by fixing. This has particular advantage in that cell samples may be stored for later analysis. In cell analytical methods, fixing i.e. preservation by crosslinking reagents such as formaldehyde and paraformaldehyde etc is often desired. However, using conventional methods to label apoptotic cells, fixing is often not possible. For example, annexin V/propidium iodide labelled samples need to be analysed freshly because the annexin needs to bind and remains bound only in the presence of high Ca buffer and the propidium iodide labelling would be misleading on fixed samples, since fixation procedures often lead to viable cells becoming permeable to the dye.

Thus, in a particular embodiment of the present invention, the antibody molecule of and for use in the invention is capable of binding to non-viable cells and capable of withstanding fixing conditions with formaldehyde.

In certain high-grade malignancies,cell death by apoptosis occurs frequently. Host immune cells (macrophages) are recruited to these tumours to engulf the apoptotic cells and elicit anti-inflammatory and immunosuppressive responses, thus protecting the tumour from anti-cancer immune attack. Work from the present inventor's laboratory has suggested that antibodies against apoptotic cells have the potential to switch the tumour macrophage response from anti-inflammatory (pro-cancer) to pro-inflammatory (anti-cancer). In this respect, the antibodies of the invention have therapeutic potential and may be used to target cell death in tumours to promote anti-tumour immunity.

Thus, the antibodies of the invention, by specifically binding to apoptotic and dead cells, may be used to enhance immune responses against such cells.

Accordingly, in an eighth aspect of the invention, there is provided a method of enhancing an immune response to an apoptotic or a dead cell, said method comprising the administration of an antibody molecule according to the third aspect of the invention or an antibody according to the fourth aspect of the invention to said cells.

By enhancing immune response, the antibodies may find use in the treatment of a number of disease conditions, for example, inflammatory conditions, where it is desirable to enhance macrophage infiltration to an inflammatory site, or in tumours. The antibodies may also be useful in enhancing wound healing.

Thus, in a ninth aspect of the invention, there is provided a method of treating inflammatory disease in a subject, said method comprising administering an antibody molecule according to the third or the fourth aspect of the invention.

In a tenth aspect of the invention, there is provided a method of treating cancer in a subject, said method comprising administering an antibody molecule according to the third or the fourth aspect of the invention.

In an eleventh aspect of the invention, there is provided a method of treating a wound or promoting wound healing in a subject, said method comprising administering an antibody molecule according to the third or the fourth aspect of the invention.

In a twelfth aspect of the invention, there is provided a pharmaceutical composition comprising an antibody molecule according to the third or the fourth aspect of the invention.

In a thirteenth aspect of the invention, there is provided an antibody molecule according to the third or the fourth aspect of the invention for use in medicine.

In a fourteenth aspect of the invention, there is provided an antibody molecule according to the third or the fourth aspect of the invention for use in the treatment of inflammatory disease.

In a fifteenth aspect of the invention, there is provided an antibody molecule according to the third or the fourth aspect of the invention for use in the treatment of cancer.

In a sixteenth aspect of the invention, there is provided an antibody molecule according to the third or the fourth aspect of the invention for use in the treatment of a wound.

In one embodiment of any one of the eighth to sixteenth aspects of the invention, the antibody molecule is an antibody molecule according to the third aspect of the invention In a seventeenth aspect of the invention, there is provided a hybridoma cell line deposited at ECACC under accession no: 07120409.

In an eighteenth aspect of the invention, there is provided a hybridoma cell line deposited at ECACC under accession no: 07120410.

In a nineteenth aspect, there is provided a nucleic acid molecule encoding an antibody molecule of the third or fourth aspect of the invention.

A twentieth aspect of the invention comprises a kit for detecting apoptotic cells in a biological sample, said kit comprising:

(i) an antibody molecule according to the third aspect of the invention, and (ii) optionally, a detectable marker for cells that have undergone lysis, or an antibody according to the fourth aspect of the invention.

In an embodiment of the twentieth aspect of the invention, the kit further comprises a label for labelling the antibody.

Preferred and alternative features of each aspect of the invention are as for each of the other aspects mutatis mutandis unless the context demands otherwise.

DETAILED DESCRIPTION

Antibody Molecules

In the context of the present invention, an antibody molecule is a molecule which has binding specificity for another molecule. An antibody molecule should be understood to refer to an immunoglobulin or part thereof or any polypeptide comprising a binding domain which is, or is homologous to, an antibody binding domain. Specific antibody molecules include but are not limited to polyclonal, monoclonal, monospecific, polyspecific antibodies and fragments thereof and chimeric antibodies comprising an immunoglobulin binding domain fused to another polypeptide. Antibody mimetics are also encompassed by antibody molecules. Antibody molecules may be intact antibodies or fragments thereof.

Intact (whole) antibodies comprise an immunoglobulin molecule consisting of heavy chains and light chains, each of which carries a variable region designated VH and VL, respectively. The variable region consists of three complementarity determining regions (CDRs, also known as hypervariable regions) and four framework regions (FR) or scaffolds. The CDR forms a complementary steric structure with the antigen molecule and determines the specificity of the antibody.

Fragments of antibodies may retain the binding ability of the intact antibody and may be used in place of the intact antibody. Accordingly, for the purposes of the present invention, unless the context demands otherwise, the term "antibody molecules" should be understood to encompass antibody fragments. Examples of antibody fragments include Fab, Fab', F (ab')2, Fd, dAb, and Fv fragments, scFvs, bispecific scFvs, diabodies, linear antibodies (see U.S. Pat. No. 5,641,870, Example 2; Zapata et al., Protein Eng 8 (10): 1057-1062 [1995]); single-chain antibody molecules; and multispecific antibodies formed from antibody fragments.

The Fab fragment consists of an entire L chain (VL and CL), together with VH and CH1. Fab' fragments differ from Fab fragments by having additional few residues at the carboxy terminus of the CH1 domain including one or more cysteines from the antibody hinge region. The F (ab') 2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993))

Further encompassed by fragments are individual CDRs.

As described above, the antibody molecules of and for use in the present invention are not limited to the IMAB6 or IMAB7 antibodies, but also extend to other antibody molecules which maintain the ability to bind apoptotic or dead cells or their components but which do not bind viable cells.

Accordingly, in one embodiment of the third aspect of the invention, the antibody molecule is an antibody molecule with binding specificity for dead and apoptotic cells, wherein the antibody molecule comprises an antigen binding domain comprising at least one of the CDRs with an amino acid sequence selected from the group consisting of Seq ID No: 1 or a variant thereof, Seq ID No: 2 or a variant thereof, Seq ID No: 3 or a variant thereof, and/or at least one of the CDRs with an amino acid sequence selected from the group consisting of Seq ID No: 4 or a variant thereof, Seq ID No: 5 or a variant thereof and Seq ID No: 6 or a variant thereof.

The amino acid sequences corresponding to Seq ID Nos: 1-6 are as follows:

```
Seq ID No: 1:
T G Y T F S S Y W I E

Seq ID No: 2:
E I L P G S G S T N Y N E K F K G

Seq ID No: 3
G G T A R A T H Y A M D Y

Seq ID No: 4:
K A S Q S V S N D V A

Seq ID No: 5:
Y A S N R Y T

Seq ID No: 6:
Q Q D Y S S P Y T
```

The antibody molecule may comprise an antigen binding domain comprising at least one of the CDRs with an amino acid sequence selected from the group consisting of Seq ID No: 1, Seq ID No: 2, Seq ID No: 3, and/or at least one of the CDRs with an amino acid sequence consisting of Seq ID No: 4, Seq ID No: 5 and Seq ID No: 6.

The antibody molecule may comprise an antigen binding domain comprising at least one of the CDRs with an amino acid sequence selected from the group consisting of Seq ID No: 1, Seq ID No: 2, Seq ID No: 3, and at least one of the CDRs with an amino acid sequence consisting of Seq ID No: 4, Seq ID No: 5 and Seq ID No: 6.

The antibody molecule may comprise an antigen binding domain comprising at least two of the CDRs with an amino acid sequence selected from the group consisting of Seq ID No: 1, Seq ID No: 2 and Seq ID No: 3, and/or at least two of the CDRs with an amino acid sequence consisting of Seq ID No: 4, Seq ID No: 5 and Seq ID No: 6.

The antigen binding domain may comprise an antibody VH domain and an antibody VL domain. In such an embodiment, the antibody VH domain may comprise at least one of the CDRs with an amino acid sequence selected from the group consisting of Seq ID No: 1, Seq ID No: 2, Seq ID No: 3 and the antibody VL domain may comprise at least one of the CDRs with an amino acid sequence consisting of Seq ID No: 4, Seq ID No: 5 and Seq ID No: 6. In one embodiment, the antibody VH domain comprises CDRs with amino acid sequences Seq ID No: 1, Seq ID No: 2 and Seq ID No: 3 as CDRs 1, 2 and 3 respectively.

In one embodiment the antibody VH domain comprises the amino acid sequence Seq ID No: 7. The antibody VL domain may comprise CDRs with amino acid sequences Seq ID No: 4, Seq ID No: 5 and Seq ID No: 6 as CDRs 1, 2 and 3 respectively.

In one embodiment of the third aspect, the antibody VL domain may comprise the amino acid sequence Seq ID No: 8. In one embodiment, the antibody molecule of the third aspect is an IMAB6 antibody molecule obtainable from the cell line deposited with ECACC under accession no: 07120409.

The amino acid sequences corresponding to Seq ID Nos: 7 and 8 are as follows:

```
Seq ID No: 7:
Q V Q L Q Q S G A E L M K P G A S V K I S C K A T

G Y T F S S Y W I E W V K Q R P G H G L E W I G E

I L P G S G S T N Y N E K F K G K A T F T A D T S

S N T A Y M Q L S S L T S E D S A V Y Y C A R G G

T A R A T H Y A M D Y W G Q G T S V T V S S

Seq ID No: 8:
D I V I T Q T P K F L L V S A G D R V T I T C K A

S Q S V S N D V A W Y Q Q K P G Q S P K L L I Y Y

A S N R Y T G V P D R F T G S G Y G T D F T F T I

S T V Q A E D L A V Y F C Q Q D Y S S P Y T F G G

G T K L E I K R
```

It is a matter of routine to the skilled person to determine the CDRs of a known antibody and thus, using the IMAB7 antibody as provided herein, the CDRs of these antibodies may easily be identified.

In one embodiment of the invention, the antibody molecule comprises an antigen binding domain comprising at least one, for example at least two or all three of the CDRs with an amino acid sequence corresponding to those of the light chain of the IMAB7 antibody (i.e. CDRL1, CDRL2, CDRL3).

In an embodiment, the antibody molecule comprises an antigen binding domain comprising at least one, for example at least two or all three of the CDRs having an amino acid sequence corresponding to that of the heavy chain of the IMAB7 antibody (i.e. CDRH1, CDRH2, CDRH3).

In one embodiment, the antibody molecule comprises an antibody $V_L$ domain having at least one of the CDRs, for example two or three CDRs having an amino acid sequence corresponding to that of CDRL1, CDRL2 and CDRL3 of IMAB7 or the antibody $V_H$ domain comprises at least one of the CDRs, for example two or three CDRs having an amino acid sequence corresponding to that of CDRH1, CDRH2 and CDRH3 of IMAB7.

In one embodiment, the antibody $V_L$ domain corresponds to that of IMAB7 and/or the antibody $V_H$ domain comprises to that of IMAB7.

In one embodiment of the invention, the antibody molecule comprises an antibody $V_H$ domain, an antibody $V_L$ domain, or both.

The CDR amino acid sequences of such antibodies in which one or more amino acid residues are modified may also be used as the CDR sequence. The modified amino acid residues in the amino acid sequences of the CDR variant are preferably 30% or less, more preferably 20% or less, most preferably 10% or less, within the entire CDR. Such variants may be provided using the teaching of the present application and techniques known in the art. The CDRs may be carried in a framework structure comprising an antibody heavy or light chain sequence or part thereof. Preferably such CDRs are positioned in a location corresponding to the position of the CDR(s) of naturally occurring VH and VL domains. The positions of such CDRs may be determined as described in Kabat et al, Sequences of Proteins of Immunological Interest, US Dept of Health and Human Services, Public Health Service, Nat'l Inst. of Health, NIH Publication No. 91-3242, 1991 and online at www.kabatdatabase.com http://immuno.bme.nwu.edu.

Furthermore, modifications may alternatively or additionally be made to the Framework Regions of the variable regions. Such changes in the framework regions may improve stability and reduce immunogenicity of the antibody.

The antibodies of and for use in the invention herein include "chimeric" antibodies in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81: 6851-6855 (1984)). Chimeric antibodies of interest herein include "primatized" antibodies comprising variable domain antigen-binding sequences derived from a non-human primate (e. g. Old World Monkey, Ape etc), and human constant region sequences.

Production of Antibodies

As discussed above, hybridomas producing IMAB6 and IMAB7 antibodies have been deposited with ECACC on 4 Dec. 2007 under accession no: 07120409 and 07120410 respectively. Other antibody molecules of and for use in the invention may be produced in any suitable way, either naturally or synthetically. Such methods may include, for example, traditional hybridoma techniques (Kohler and Milstein (1975) Nature, 256 :495-499), recombinant DNA techniques (see e.g. U.S. Pat. No. 4,816,567), or phage display techniques using antibody libraries (see e.g. Clackson et al. (1991) Nature, 352: 624-628 and Marks et al. (1992) Bio/Technology, 10: 779-783). Other antibody production techniques are described in Antibodies: A Laboratory Manual, eds. Harlow et al., Cold Spring Harbor Laboratory, 1988.

Traditional hybridoma techniques typically involve the immunisation of a mouse or other animal with an antigen in order to elicit production of lymphocytes capable of binding the antigen. The lymphocytes are isolated and fused with a myeloma cell line to form hybridoma cells which are then cultured in conditions which inhibit the growth of the parental myeloma cells but allow growth of the antibody producing hybridoma cells. The hybridoma may be subject to genetic mutation, which may or may not alter the binding specificity of antibodies produced. Synthetic antibodies can be made using techniques known in the art (see, for example, Knappik et al, J. Mol. Biol. (2000) 296, 57-86 and Krebs et al, J. Immunol. Meth. (2001) 2154 67-84.

Modifications may be made in the VH, VL or CDRs of the antibody molecules, or indeed in the FRs using any suitable technique known in the art. For example, variable VH and/or VL domains may be produced by introducing a CDR, e.g. CDR3 into a VH or VL domain lacking such a CDR. Marks et al. (1992) Bio/Technology, 10: 779-783 describe a shuffling technique in which a repertoire of VH variable domains lacking CDR3 is generated and is then combined with a CDR3 of a particular antibody to produce novel VH regions. Using analogous techniques, novel VH and VL domains comprising CDR derived sequences of the present invention may be produced.

Accordingly, antibody molecules for use in the invention may be produced by a method comprising: (a) providing a starting repertoire of nucleic acids encoding a variable domain, wherein the variable domain includes a CDR1, CDR2 or CDR3 to be replaced or the nucleic acid lacks an encoding region for such a CDR; (b) combining the repertoire with a donor nucleic acid encoding an amino acid sequence having the sequence as shown as Seq ID No: 1, 2, 3, 4, 5 or 6 herein such that the donor nucleic acid is inserted into the CDR region in the repertoire so as to provide a product repertoire of nucleic acids encoding a variable domain; (c) expressing the nucleic acids of the product repertoire; (d) selecting a specific antigen-binding fragment specific for apoptotic or dead cells; and (e) recovering the specific antigen-binding fragment or nucleic acid encoding it.

Alternative techniques of producing variant antibodies of the invention may involve random mutagenesis of gene(s) encoding the VH or VL domain using, for example, error prone PCR (see Gram et al, 1992, P.N.A.S. 89 3576-3580. Additionally or alternatively, CDRs may be targeted for mutagenesis e.g. using the molecular evolution approaches described by Barbas et al 1991 PNAS 3809-3813 and Scier 1996 J Mol Biol 263 551-567.

Having produced such variants, antibodies and fragments may be tested for desired activity, for example the ability to selectively bind non-viable apoptotic and/or dead cells.

In some embodiments, antibodies of the invention may be labelled. Labels which may be used include radiolabels, enzyme labels such as horseradish peroxidase, alkaline phosphatase, or biotin. The detectable reagent for use in the invention may be detected using any suitable method in the art. For example, in one embodiment, the reagent may be detected using a reagent-specific antibody. In another embodiment, the reagent may be labelled. Any suitable label may be used. For example, labels which may be used include but are not limited to proteins such as ferritin, biotin, avidin and streptavidin and derivatives thereof, fluorescent markers, for example fluorescein, radioactive labels such as $^{125}I$, $^{131}I$, $^{32}P$, or $^{35}S$, enzymes such as alcohol dehydrogenase, peroxidase or alkaline phosphatase, dyes such as Evans Blue or Coomassie Brilliant Blue, detectable metals or detectable immunoglobulins.

Nucleic Acid

In one embodiment, the invention provides a nucleic acid molecule which encodes an antibody of the invention.

Nucleic acid of and for use in the present invention may comprise DNA or RNA. It may be produced recombinantly, synthetically, or by any means available to those in the art, including cloning using standard techniques.

The nucleic acid may be inserted into any appropriate vector. A vector comprising a nucleic acid of the invention forms a further aspect of the present invention. In one embodiment the vector is an expression vector and the nucleic acid is operably linked to a control sequence which is capable of providing expression of the nucleic acid in a host cell. A variety of vectors may be used. For example, suitable vectors may include viruses, e. g. vaccinia virus, adenovirus, baculovirus; yeast vectors, phage, chromosomes, artificial chromosomes, plasmids, or cosmid DNA.

The vectors may be used to introduce the nucleic acids of the invention into a host cell. A wide variety of host cells may be used for expression of the nucleic acid of the invention. Suitable host cells for use in the invention may be prokaryotic or eukaryotic. They include bacteria, e.g. *E. coli*, yeast, insect cells and mammalian cells. Mammalian cell lines which may be used include Chinese hamster ovary cells, baby hamster kidney cells, NS0 mouse myeloma cells, monkey and human cell lines and derivatives thereof and many others.

A host cell strain that modulates the expression of, modifies, and/or specifically processes the gene product may be used. Such processing may involve glycosylation, ubiquitination, disulfide bond formation and general post-translational modification.

Accordingly, the present invention also provides a host cell, which comprises one or more nucleic acid or vectors of the invention.

Also encompassed by the invention is a method of production of an antibody molecule of the invention, the method comprising culturing a host cell comprising a nucleic acid of the invention under conditions in which expression of the antibody molecules from the nucleic acid occurs and, optionally, isolating and/or purifying the antibody molecule.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 5th ed., Ausubel et al. eds., John Wiley & Sons, 2005 and, Molecular Cloning: a Laboratory Manual: $3^{rd}$ edition Sambrook et al., Cold Spring Harbor Laboratory Press, 2001.

Separation Methods

As described above, the present invention encompasses methods of separating cells or cell components from samples, such as cell culture preparations, blood, serum, or any other biological sample. In such methods, the antibody molecules of and for use in the invention may be provided conjugated to a substrate to enable separation of the antibody molecules once bound to a target cell or cell component.

Any suitable solid substrate, which can be used in immobilisation or separation techniques, may be used. Such substrates may be in the form of beads, sheets, particles, membranes etc. In one embodiment, the substrate is made of a particular material in order to enhance binding capacity. In a particular embodiment of the invention, the antibody molecules are provided conjugated to magnetic particles or beads. Such magnetic particles or beads, by application of a magnetic field, may be readily separated from a sample.

Antibodies and fragments thereof, may be coupled to substrates such as magnetic particles using any suitable technique known in the art. Coupling may be direct or indirect. In one embodiment, antibodies may be coupled covalently to a substrate, for example, via functional groups present on the substrates. Such groups may include hydroxyl groups, carboxyl groups, amino groups, epoxy groups or aldehyde groups.

Particular methods which may be used include the coupling of antibodies to substrates having the sulphonyl esters. The sulphonyl esters react with amino groups or —SH groups on antibodies to give $CH_2$—NH or $CH_2$—S—. Another method of coupling an antibody to a substrate is the provision of a carboxylic group on the substrate, which, by activation with carbodiimide and N-hydroxysulphosuccinimide to form amino bonds between the support and the antibody. Supports containing amino groups may be activated using glutaraldehyde to form covalent bonds with amino groups of an antibody.

As described above, in particular embodiments of the invention, the antibodies are brought into contact with target cells or cell components and separated without the need for secondary antibodies. In such embodiments, the antibodies may be provided coupled to substrates before coming into contact with the target cell or cell components. In alternative embodiments, the antibody which binds the target cell or cell component may be separated by means of a secondary antibody or indeed a binding partner as such as (strept)avidin if any antibody is labelled with biotin.

The methods of the invention may be used for positive cell selection or negative cell selection. In positive cell selection, cells of interest are bound and removed from a sample. In contrast, in negative cell selection contaminating cells, such as dying or dead cells or indeed components from dying or dead cells, are removed from a sample.

As described above, a particular embodiment of the present invention is concerned with removal of dead, dying or apoptotic cells for a cell sample, such as a cell culture sample, to optimise the number of live cells in the sample. The methods of the invention may thus be used in enrichment strategies of cell culture. In a particular embodiment, the invention involves magnetic activated cell sorting to enrich cell culture by removal of non-viable cells and components.

In some circumstances, in particular positive selection protocols, it will be desired to separate bound cells (or cell components) from the antibody molecule. Several techniques to achieve such separation are well-known in the art. Such techniques may be, for example, mechanical (for example see U.S. Pat. Nos. 5,215,927 and 5,225,353) or enzymatic, for example using papain or chymopapain.

Treatment

Treatment" includes any regime that can benefit a human or non-human animal. The treatment may be in respect of an existing condition or may be prophylactic (preventative treatment). Treatment may include curative, alleviation or prophylactic effects.

"Treatment of cancer" includes treatment of conditions caused by cancerous growth and/or vascularisation and includes the treatment of neoplastic growths or tumours. Examples of tumours that can be treated using the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, prostate, cervical and ovarian carcinoma, non-small cell lung cancer, hepatocellular carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, astrocytomas, gliomas and retinoblastomas.

Inflammatory conditions for which the present invention may find use include, but are not limited to, inflammatory conditions such as peritonitis, arthritis, pleurisy, lung fibrosis, systemic sclerosis and chronic obstructive pulmonary disease (COPD). Other conditions for which the invention may be useful include inflammatory lung disease, atopic dermatitis, NERDS (nodules eosinophilia, rheumatism, dermatitis and swelling), pulmonary fibrosis, inflammatory bowel disease (IBD), vasculitic granulomatous diseases including polyarteritis and Wegeners granulomatosis, sarcoidosis, idiopathic pulmonary fibrosis, auto-immune diseases, eosinophilic pneumonia, reperfusion damage caused by myocardial infarction, atheroma; glomerular nephritis; rheumatoid arthritis, gout Pharmaceutical Compositions Pharmaceutical compositions according to the present invention, and for use in accordance with the present invention may comprise, in addition to active ingredients, a pharmaceutically acceptable excipient, a carrier, buffer stabiliser or other materials well known to those skilled in the art (see, for example, (Remington: the Science and Practice of Pharmacy, 21$^{st}$ edition, Gennaro A R, et al, eds., Lippincott Williams & Wilkins, 2005.). Such materials may include buffers such as acetate, Tris, phosphate, citrate, and other organic acids; antioxidants; preservatives; proteins, such as serum albumin, gelatin, or immunoglobulins; hydrophilic polymers such aspolyvinylpyrrolidone; amino acids such as glycine, glutamine, asparagine, histidine, arginine, or lysine; carbohydrates; chelating agents; tonicifiers; and surfactants.

The pharmaceutical compositions may also contain one or more further active compounds selected as necessary for the particular indication being treated, preferably with complementary activities that do not adversely affect the activity of the composition of the invention. The active ingredients may be administered via microspheres, microcapsules liposomes, other microparticulate delivery systems. For example, active ingredients may be entrapped within microcapsules which may be prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. For further details, see Remington: the Science and Practice of Pharmacy, 21$^{st}$ edition, Gennaro A R, et al, eds., Lippincott Williams & Wilkins, 2005.

Sustained-release preparations may be used for delivery of active agents. Suitable examples of sustained-release preparations include semi-permeable matrices of solid hydrophobic polymers containing the antibody, which matrices are in the form of shaped articles, e. g. films, suppositories or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L glutamate, non-degradable ethylene-vinyl acetate, degradable lactic acid-glycolic acid copolymers, and poly-D-(−)-3-hydroxybutyric acid.

Dose

The antibodies of and for use in the invention, as appropriate, are suitably administered to an individual in a "therapeutically effective amount", this being sufficient to show benefit to the individual. The actual dosage regimen will depend on a number of factors including the condition being treated, its severity, the patient being treated, the agents being used, and will be at the discretion of the physician.

BRIEF DESCRIPTION OF THE DRAWINGS

The invention will now be described further in the following non-limiting examples. Reference is made to the accompanying drawings in which:

FIG. 1 illustrates differential labelling of PI-negative BL cells with IMAB6 and IMAB7 following induction of apoptosis by staurosporine;

FIG. 2 illustrates identification of 'viable' and dead BL cells using light scatter and PI fluorescence analysis;

FIG. 3 illustrates differential labelling of PI-negative (apoptotic) and PI-positive (dead) BL cells with IMAB6 and IMAB7 following induction of apoptosis by staurosporine;

FIG. 4 illustrates differential labelling of BL cells in 'viable' and dead light-scatter zones with IMAB6 and IMAB7 following induction of apoptosis by staurosporine;

FIG. 5 illustrates gradual appearance of apoptotic cells in the 'viable' light scatter zone following induction of apoptosis in BL cells using staurosporine;

FIG. 6 illustrates gradual appearance of apoptotic cells in the 'viable' light scatter zone following induction of apoptosis in BL cells after frozen storage;

FIG. 7 illustrates comparable reactivities of annexin V and IMAB6 on apoptotic thymocytes;

FIG. 8 illustrates comparable reactivities of annexin V and IMAB6 on PI-negative, apoptotic BL cells;

FIG. 9 illustrates IMAB6 and IMAB7 react with phospholipids phosphatidylserine (PS) and phosphatidylglycerol (PG);

FIG. 10 illustrates direct depletion of dead cells by IMAB6-coupled magnetic particles; FIG. 10A shows a bar chart illustrating the percentage of cells positive for trypan blue staining in cell samples depleted of dead cells by three different methods;. FIG. 10B illustrates the percentage of dead cells as assessed by FACS in a cell sample after depletion of dead cells using the same methods as in FIG. 10A;

FIG. 11 illustrates interactions of cells with magnetic particles for dead-cell depletion are not improved by sample rotation;

FIG. 12 illustrates efficient depletion of dead BL cells by IMA6-coupled magnetic particles in complete culture medium at 37° C.;

FIG. 13 illustrates depletion of dead BL cells by IMA6-coupled magnetic particles in complete culture medium at 37° C.: effect of time of interaction;

FIG. 14 illustrates direct dead-cell depletion from BL cultures by IMAB6-coupled 300 and 500 nm magnetic particles;

FIG. 15 illustrates the results of an experiment to demonstrate the use of IMAB-6 to separate viable and dead cells by flow cytometry;

FIG. 16 illustrates detection of microparticles released from apoptotic cells by IMAB-6 labelling;

FIG. 17 illustrates separation of microparticles, blebs and apoptotic cells;

FIG. 19 illustrates IMAB-6 Heavy Chain V region nucleic acid and amino acid sequences and show the sequences of CDRH1, CDRH2, and CDRH3;

FIG. 20 illustrates IMAB-6 Light Chain V region and Constant region nucleic acid and amino acid sequences and show the sequences for CDRL1, CDRL2 and CDRL3.

EXAMPLES

Figure 18:
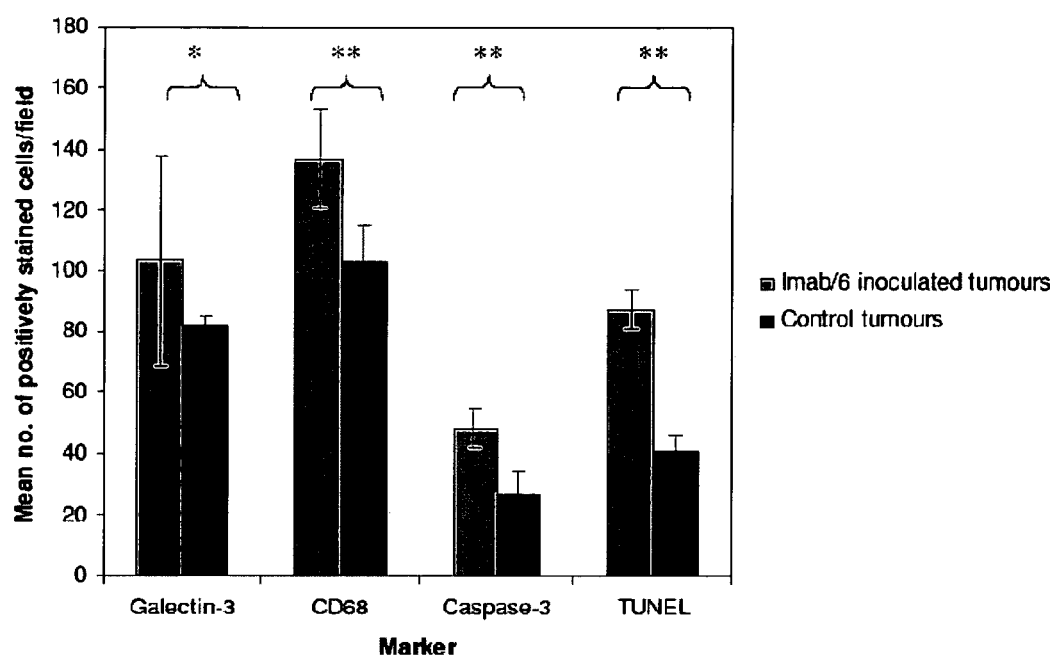
FIG. 18 illustrates that IMAB6 modulates the immune response to apoptotic cells in vivo.

1. IMAB6 and IMAB7 Recognise Different Epitopes on Cells Undergoing Apoptosis and Discriminate between Viable, Apoptotic and Dead Cells Hybridomas producing the IMAB6 and IMAB7 monclonal antibodies were generated by immunization of balb/c mice and fusion of immune splenocytes with NS0 myeloma cells using procedures that are standard to those skilled in the art. The isotypes of the antibodies were determined to be IgM in both cases.

Example 1

The human Burkitt lymphoma (BL) cell line BL2 was induced to undergo rapid, synchronous apoptosis by stimulation with the protein kinase inhibitor, staurosporine (1 µM) at 37° C. for the indicated times (FIG. 1) between 30 minutes and 4 hours. Staurosporine is a well-known inducer of apoptosis in many cell types (see later for demonstration of annexin V binding to apoptotic BL cells induced by the same mechanism). Cells were then harvested and labelled with IMAB6 or IMAB7 antibodies by standard procedures. Antibodies were prepared from cell-free supernatant preparations of IMAB6 or IMAB7 hybridoma cultures growing in RPMI 1640 medium containing 10% fetal calf serum (FCS). IMAB6 was concentrated using a Centriplus ultrafiltration unit (Millipore; MW cut-off 100,000 kDa); IMAB7 was prepared by ammonium sulphate precipitation followed by dialysis against phosphate buffered saline (PBS, free of $Ca^{2+}$ and $Mg^{2+}$). Antibodies (40 µl) were added to BL2 cells ($5 \times 10^5$) and incubated at 4° C. for 30 minutes. Cells were washed in PBS containing 5% normal goat serum (NGS) and subsequently incubated for a further 15 minutes at 4° C. in 40 µl secondary antibody (goat anti-mouse IgG (whole molecule) fluorescein isothiocyanate (FITC) conjugate (GAM), Sigma, 1:25 in PBS/5% NGS). After a further wash in PBS/5% NGS, cells were resuspended in the same buffer containing propidium iodide (PI, Sigma, 0.8 µg/ml) and analysed on the Beckman Coulter XL flow cytometer using procedures that are standard to those skilled in the art.

FIG. 1 shows fluorescence histograms of the stained cell preparations that are PI negative (ie retain plasma membrane integrity) at the indicated times after staurosporine treatment; GAM (red histograms) denotes background labelling. Virtually all cells become positively stained with IMAB6 by 3 hours following staurosporine stimulation, whereas IMAB7 fails to label any of the cells at this time.

Further flow cytometric analyses (FIGS. 3, 4) indicate that, while IMAB7 fails to bind to cells that retain intact plasma membranes, this antibody binds to cells that have become lysed (this is a late characteristic of the apoptosis programme in vitro). It has previously been demonstrated that flow cytometry allows discrimination of dead and viable or apoptotic BL cells in unstained preparations using light scatter parameters (Dive, C., C. D. Gregory, et al. (1992). "Analysis and discrimination of necrosis and apoptosis (programmed cell death) by multiparameter flow cytometry." *Biochimica et Biophysica Acta* 1133(3): 275-285.). To illustrate this, FIG. 2 demonstrates that BL cells can be subdivided, on the basis of forward and side light scatter, into cell population zones that represent dead or 'viable' cells (left panel, FIG. 2). PI fluorescence analysis indicates that cells falling into the dead zone are PI-positive, while those falling into the 'viable' zone are PI-negative (right panel, FIG. 2). In fact, the 'viable' zone contains either truly viable cells, or dying cells, ie cells that are undergoing apoptosis but retain plasma membrane integrity. Such dying cells can be visualised using either annexin V or IMAB6 (but not IMAB7).

Example 2

FIG. 3 compares the PI-negative and PI-positive BL cell populations after treatment with staurosporine for 3 hours. The fluorescence histograms of these cells show that both PI-positive (dead) and PI-negative (apoptotic, dying) cells label with IMAB6, whereas PI-positive, but not PI-negative, cells label with IMAB7.

These results are confirmed in FIG. 4, in which the IMAB6/7 labelling properties of the same staurosporine treated cells are analysed according to light scatter features. As shown, both dead zone and 'viable' zone (in this case predominantly apoptotic) cells label with IMAB6, whereas dead zone, but not 'viable' zone, cells label with IMAB7.

Taken together, these results demonstrate that IMAB6 and IMAB7 bind to different epitopes on dying (apoptotic) and dead cells and that these antibodies can be used to discriminate (1) viable, (2) dying and (3) dead cells.

2. IMAB6 can be Used to Monitor Stages of Apoptosis Induced by Multiple Stimuli in Different Species and Labels the same Cells as Annexin V

Example 3

FIG. 5 shows BL2 cells stimulated with staurosporine and labelled with IMAB6 as described above. In this case the bound IMAB6 is visualised using goat anti-mouse IgG (whole molecule) phycoerythrin conjugate (Sigma, 1:25 in PBS/5% NGS) as the secondary antibody. This experiment demonstrates the gradual appearance of apoptotic cells, from around 5% at time zero, through 26% at 1 hour, to over 95% at 3 hours in the 'viable' light scatter zone.

Example 4

In FIG. 6, apoptosis was triggered in BL cells following thawing after frozen storage. BL2 cells suspended in FCS containing 5% dimethyl sulphoxide (DMSO) were frozen down to −80° C. following standard procedures at a rate of approximately 1° C. per minute. The cells were subsequently thawed rapidly at 37° C., washed to remove DMSO and resuspended in culture medium (RPMI 1640 containing 2 mM L-glutamine and 10% FCS). At the times indicated, the cells were labelled with IMAB6 as described above and analysed by flow cytometry. As shown in FIG. 6, the gradual appearance of apoptotic cells in the 'viable' light scatter zone is revealed by IMAB6 labelling prior to the appearance of any significant numbers of cells in the dead zone.

Example 5

BL2 cells are a human tumour cell line of B-cell origin. FIG. 7 demonstrates that IMAB6 also binds to apoptotic primary mouse thymocytes, demonstrating that its reactivity is not restricted to (a) human cells, (b) malignant cells, (c) cell lines or (d) B-lineage cells. The thymus was carefully dissected from a balb/c mouse and a suspension of thymocytes was isolated by standard procedures after grinding the organ between the frosted ends of two glass microscope slides. Thymocytes were induced to undergo apoptosis by incubation with dexamethasone (100 nM) overnight. Thymocytes were subsequently labelled with (1) IMAB6 and FITC-conjugated GAM as described or with (2) FITC-conjugated annexin V (Bender) according to the manufacturer's instructions, the annexin V conjugation requiring continuous presence of 2.5 mM $Ca^{2+}$ during and after the annexin V binding stage (note: as is demonstrated by the labelling methodology described above, IMAB6 has no such requirement for $Ca^{2+}$, either in the labelling process or in the maintenance of bound IMAB6 on labelled cells as is the case for annexin V). As shown in FIG. 7, flow cytometric analysis of labelled cells reveals comparable reactivities (blue histograms) of annexin V and IMAB6 on apoptotic thymocytes. Red histograms denote background fluorescence (unlabelled thymocytes in the case of annexin V and thymocytes exposed to secondary antibody alone in the case of IMAB6).

Example 6

FIG. 8 further demonstrates that IMAB6 has comparable reactivity to annexin V. In this experimental series, BL2 cells were induced into apoptosis using staurosporine and labelled with either IMAB6/FITC or annexin V/FITC, further labelled with propidium iodide using the methods described and analysed by flow cytometry. Annexin V labelling of cells in the absence of propidium iodide staining is commonly used to assess apoptosis. FIG. 8 compares the reactivities of annexin V and IMAB6 on PI-negative cells undergoing apoptosis, with percentages of IMAB6-(black) and annexin V-positive cells (chequered) at various times following stimulation by staurosporin shown. The results demonstrate that the reactivity of IMAB6 closely parallels that of annexin V and the antibody appears to be marginally more sensitive during the early phase of the time course.

3. IMAB6 and IMAB7 Bind to Phospholipids

Example 7

The specificities of IMAB6 were tested against phospholipids in ELISA using standard approaches. In brief, wells of ELISA plates were coated with phospholipids (a) phosphatidylserine (PS), (b) phosphatidylglycerol (PG) or (c) PS and PG in combination. Phospholipid stocks (1 mM in chloroform) were diluted to 100 µg/ml and 50 µl aliquots were evaporated to dryness in ELISA plate wells at room temperature. Wells were blocked with 100 µl PBS containing 0.3% gelatin from fish skin (Sigma) for 2 hours, washed 3× with PBS and then exposed to 50 µl IMAB6 or IMAB7, each diluted 1:10 in PBS/gelatin, for 1 hour at 37° C. IMAB6 and IMAB7 antibodies were cell-free supernatants of the corresponding hybridoma cells growing in either a Celline bioreactor (Integra, IMAB6) or tissue culture flask (IMAB7) in RPMI supplemented with heat-inactivated FCS. Following a further 3 washes in PBS, wells were exposed to goat-anti-mouse IgM-peroxidase antibody conjugate (Sigma, 1:1000 in PBS/gelatin) for a further 1 hour at 37° C. Following 3× PBS washes, wells were incubated with peroxidase substrate (SIGMAFAST™ OPD (o-Phenylenediamine dihydrochloride), Sigma) for 35 minutes at room temperature, blocked with $H_2SO_4$, and read at 492 nm using an Anthos 96-well plate reader. As shown in FIG. 9, IMAB6 and IMAB7 react with both PS and PG. In this assay, background absorbance values were recorded from wells that received no phospholipids but were otherwise treated identically. The higher absorbances achieved with the IMAB6 antibody preparation are due to the higher titre of antibody obtained from the Celline bioreactor than from normal flask culture.

Because of their identical reactivities in the ELISA but not on cells, taken together with the flow cytometric data, these results demonstrate that IMAB6 and IMAB7 specify different epitopes on PS and/or PG that are differentially exposed on cells during apoptosis.

4. IMAB6 can be Directly Coupled to Super-Paramagnetic Particles to Remove Dead Cells Efficiently by Direct Depletion Example 8

The human B cell line, BL2, was depleted of dead cells by three methods:

Method 1: by primary labelling of dying and dead cells with monoclonal antibody IMAB6 followed by separation using superparamagnetic 300 nm particles coupled with goat anti-mouse immunoglobulin (GAM) to deplete dying/dead cells on a magnet;

Method 2: by direct binding of superparamagnetic 300 nm particles coupled with IMAB6 and then depleting dying/dead cells on a magnet;

Method 3: by standard density gradient centrifugation on Ficoll-Paque. For each method, after separation, the depleted sample was stained using trypan blue, 0.2% in PBS, and the percentage of dead cells remaining in the sample assessed microscopically. Parallel samples were tested using a flow cytometer (XL, Beckman Coulter), with dead cells defined by light scatter properties as described (Dive, C., C. D. Gregory, et al. (1992). "Analysis and discrimination of necrosis and apoptosis (programmed cell death) by multiparameter flow cytometry." *Biochimica Et Biophysica Acta* 1133(3): 275-285.). The results are shown in FIG. 10.

Carboxyl-activated 300 nm super-paramagnetic particles (Ademtech, Pessac, France) were coupled with either IMAB6 (alone or in the presence of bovine lactoferrin, LF) or goat anti-mouse immunoglobulin (Sigma Aldrich, UK) using EDC (1-ethyl-3-[3-dimethylaminopropyl]carbodiimide hydrochloride, Pierce, Rockford Ill.) according to the particle manufacturer's instructions. For magnetic separation, cells (100 µl, 7.5×10$^7$/ml)—either unlabelled or pre-labelled with IMAB6 antibody for 30 minutes at 4° C. followed by washing—were resuspended in PBS ($Ca^{2+}$ and $Mg^{2+}$ free) with 0.5% bovine serum albumin (BSA) and 2mM EDTA ("Magsep buffer") containing 0.1 mg GAM- or IMAB6-coupled magnetic particles and incubated in a 1.5 ml Eppendorf tube at 4° C. for 30 minutes with gentle rotation. Cells and particles were subsequently gently resuspended in 0.5 ml PBS/BSA/EDTA (Magsep buffer) and the tube placed on a magnet (Ademtech Adem-Mag SV) for 4 minutes after which time the cells remaining in suspension were removed and tested for viability as described above. Density gradient separation on Ficoll-Paque PLUS (Amersham) was carried out according to the manufacturers instructions.

As can be seen from both FIGS. 10A and 10B, IMAB6 antibodies directly coupled to super-paramagnetic 300 nm particles provided very efficient depletion of dead cells from the initial sample, the efficiency being approximately as good as standard density gradient centrifugation (Method 3). The presence of EDTA in the interaction/separation buffer demonstrates that the efficient dead-cell depletion in this system has no $Ca^{2+}$ requirement.

In this example, Method 1 (pre-labelling of cells using IMAB6 and attempted magnetic depletion using magnetic particles coupled with GAM) may have failed because of inefficient coupling of the secondary antibody to the magnetic particles. The apparent greater number of dead cells in FIG. 10A in the Method 1 samples is not significant. This example does not prove that indirect methods using IMAB6 are necessarily ineffective—it is possible that they could be improved by enhanced particle coupling. The example clearly demonstrates that the direct method is very effective. The presence of LF along with IMAB6 failed to improve particle efficacy in dead-cell depletion.

Example 9

Direct depletion of dead cells by IMAB6-coupled magnetic particles requires efficient interactions between particles and dead cells prior to the depletion step with the magnet. In this example, the effect of co-incubating cells and particles under stationary conditions or with gentle rotation is documented. Cells and particles were treated as in Example 8 with some modifications: the interaction/separation buffer was as above, PBS/BSA/EDTA Magsep buffer, cells were at $5\times10^7$/ml and interaction with 0.05 mg IMAB6-coupled 300 nm particles was carried out at 4° C. for 10, 20 or 40 minutes either in static tubes or with continuous gentle rotation. Dead cells were enumerated microscopically as trypan blue-positive as described above. As shown in FIG. 11, rotation failed to promote efficiency in depletion of dead cells. Indeed, rotation of the cells had a negative effect on viability (the No Beads' samples were incubated either static, or on the rotor for the full 40 minutes).

5. Direct Depletion of Dead Cells Using IMAB6-Coupled Magnetic Particles Under in vitro Physiological Conditions Example 10

In this example, the effect of varying environmental conditions on direct dead-cell depletion by IMAB6-coupled particles is demonstrated. Specifically both temperature and buffer medium are varied. The methodology is broadly similar to that described in earlier examples with some modifications. In brief, BL cells ($5\times10^7$/ml) were incubated in static 1.5 ml tubes with 0.05 mg IMAB6-coupled 300 nm particles in Magsep buffer or in complete BL culture medium ('BL med' in FIG. 12: RPMI supplemented with 10% FCS) for 45 minutes at 4° C., room temperature (RT) or 37° C. Control cells without beads were incubated at 37° C. Following separation on the magnet (4-5 minutes), negatively selected cells were subjected to flow cytometric analysis of PI positive cells after labelling with 0.8 µg/ml PI.

As shown in FIG. 12, in Magsep buffer (black bars), only minor changes in efficiency of dead-cell depletion (reduction in PI-positive cells) were obtained by temperature variation. However, when cells were subjected to depletion steps in complete BL culture medium (chequered bars), optimal conditions were attained at physiological temperature, 37° C. These results demonstrate that dead cells can be effectively depleted from cell cultures directly by IMAB6-coupled particles at optimal physiological conditions in complete culture medium.

Example 11

Furthermore, as shown in FIG. 13, using identical methodology to that described for the previous example, variation of the time of interaction between cells and magnetic particles in complete BL medium at 37° C. indicated that optimal efficiency was approached when an interaction time of 40-60 minutes was adopted prior to magnetic separation.

Example 12

In this example, (a) two magnetic particle sizes are compared, (b) the effect of IMAB6 antibody concentration in the particle coupling reaction is tested, and (c) the effect of two sequential magnetic separation steps documented. Methodologies are similar to those described in the examples above except that batches of both 300 nm and 500 nm carboxyl-activated particles (Ademtech) were used in two coupling reactions for each size of particle, with the second coupling reaction receiving twice the IMAB6 antibody concentration as the first. The batches are demarcated 300/1, 300/2, 500/1 and 500/2 in FIG. 14. Using 0.1 mg particles per sample, with BL cells co-incubated with particles in complete culture medium at 37° C for 40 minutes, two modes of interaction/separation were compared. The first mode was as described in the examples above, in 1.5 ml polypropylene eppendorf tubes in the Ademtech magnet (Adem-Mag SV); the second mode was in 12×75 mm Falcon 2052 FACS tubes (Becton Dickinson) following the generic magnetic cell-separation protocol provided by StemCell Technologies using its EasySep magnet. In each case, cells were stained with PI and analysed by flow cytometry after one or two magnetic separations.

As shown in FIG. 14, PI-positive dead cells were depleted by both 300 and 500 nm particles with similar efficiencies using the two types of vessel, eppendorf tube and FACS tube. 300 nm particles coupled with higher IMAB6 antibody concentration worked most effectively. Most dead cells were depleted during the first magnetic separation, with a second depletion step having little effect on the negatively selected population.

Example 13

Use of IMAB-6 to Separate Viable and Dead Cells by Flow Cytometry

A mixture of approximately 50% viable and 50% dead Burkitt lymphoma cells (as assessed by propidium iodide (PI) fluorescence) were incubated with IMAB-6 followed by FITC-coupled secondary antibody and subjected to fluorescence-activated cell sorting. The results are shown in FIG. 15. The percentage of dead cells is shown before (58.5%) and after (4.39%) sorting of IMAB-6-negative cells. This demonstrates that IMAB-6 can be used effectively to sort viable from dead cells.

Example 14

Detection of Microparticles Released from Apoptotic Cells by IMAB-6 Labelling

Subcellular microparticles (<1 micron) were collected following induction of Burkitt lymphoma cells with staurosporine for 3 hours after which they were immunostained with IMAB-6/FITC. Labelling of cell-derived microparticles (MP) was carried out using ultracentrifugation washing steps (100,000 g, 20 mins). MP were prepared by incubation of staurosporine-treated BL cells in serum-free medium for 3 hours, removal of cells by gentle centrifugation (50 g) and subsequent ultracentrifugation (100,000 g, 20 mins, 4° C.) of cell-free supernatants. MP were estimated, using fluorescent bead standards (Beckman-Coulter, Buckinghamshire, UK), to be in the range 100-1000 nm. The results are shown in FIG. 16. Upper panels show the light scatter properties of cells and microparticles. Lower panels show selective gating of microparticles. Left, log light scatter; middle, IMAB-6 staining in red; right, backgating of IMAB-6-stained particles in relation to light scatter, demonstrating labelling across a range of microparticle sizes of <1 micron.

Example 15

Separation of Microparticles, Blebs and Apoptotic Cells

IMAB-6 was adsorbed onto polystyrene and exposed to a mixture of viable and apoptotic hybridoma cells, and apoptotic cell-derived blebs and microparticles. The results are shown in FIG. 17. Note amongst the "sand" of microparticles, the capture of blebs and apoptotic cells (arrows).

Example 16

Modulation of Immune Response to Apoptotic Cells in vivo

Xenografts of Burkitt lymphoma were generated in SCID mice as described (Ogden et al (2005) J. Immunol. 174, 3015) and inoculated with PBS (Control) or IMAB-6 antibody. Subsequently, levels of apoptosis (Caspase-3; TUNEL) and macrophage infiltration (CD68, Galectin-3) were assessed by morphometric analysis of immuno-stained histological sections. The results are shown in FIG. 18. Note the effects of IMAB-6: (1) significantly increased levels of apoptosis and (2) significantly increased levels of infiltrating macrophages. One non-limiting interpretation of these results is that IMAB-6 inhibits the clearance of apoptotic cells in the tumours resulting in enhanced macrophage infiltration.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

---

The invention claimed is:

1. An antibody molecule with binding specificity for non-viable cells, wherein the antibody molecule comprises an antigen binding domain comprising a $V_L$ domain comprising the CDRs with amino acid sequences of SEQ ID No: 4, SEQ ID No: 5 and SEQ ID No: 6 as CDRs $L_1$, $L_2$ and $L_3$ respectively and a $V_H$ domain comprising the CDRs with amino acid sequences of SEQ ID No: 1, SEQ ID No: 2 and SEQ ID No: 3 as CDRs $H_1$, $H_2$ and $H_3$ respectively.

2. The antibody molecule according to claim 1 wherein the antibody $V_H$ domain comprises the amino acid sequence SEQ ID No: 7.

3. The antibody molecule according to claim 1 wherein the antibody $V_L$ domain comprises the amino acid sequence SEQ ID No: 8.

4. The antibody molecule according to claim 1 wherein the antibody molecule is an IgM, IgG, IgA or IgE molecule.

5. The antibody molecule of claim 1 wherein the antibody molecule is an IMAB6 antibody molecule obtainable from the cell line deposited with ECACC under accession no: 07120409.

6. A method of separating a target cell or cell component from/in a sample, said method comprising:
   contacting said sample with the antibody molecule according to claim 1;
   allowing said antibody molecule to form a conjugate with said target cell or cell component;
   and separating said conjugate from said sample wherein said cell is a non-viable cell.

7. The method according to claim 6, wherein said method is a method of separating non-viable cells or cell components from viable cells.

8. A method of enriching a population of viable cells in a sample, said method comprising removal of non-viable cells from said sample using the method according to claim 6.

9. A pharmaceutical composition comprising the antibody molecule according to claim 1.

10. A method of enhancing an immune response to a non-viable cell, comprising administering the antibody molecule according to claim 1.

11. The method of claim 6, wherein the antibody molecule is an IgM antibody and the separating step does not involve the use of a secondary binding moiety.

12. A kit for detecting apoptotic cells in a sample, said kit comprising:
    (i) the antibody molecule according to claim 1; and
    (ii) a detectable marker for cells that undergone lysis.

13. A method of detecting non-viable cells or cell components thereof in a biological sample, the method comprising the steps of:
    contacting the sample with the antibody molecule according to claim 1;
    and detecting binding of the antibody molecule to said cells or cell components of the sample.

14. The method according to claim 13 wherein the antibody molecule comprises an antibody bound to a magnetic bead.

* * * * *

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Thr Gly Tyr Thr Phe Ser Ser Tyr Trp Ile Glu
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Glu Ile Leu Pro Gly Ser Ser Thr Asn Tyr Asn Glu Lys Phe Lys Gly
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Gly Gly Thr Ala Arg Ala Thr His Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 4

Lys Ala Ser Gln Ser Val Ser Asn Asp Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Tyr Ala Ser Asn Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Asp Tyr Ser Ser Pro Tyr Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic

<400> SEQUENCE: 7

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Ala Arg Ala Thr His Tyr Ala Met Asp Tyr Trp
            100                 105                 110

Gly Gln Gly Thr Ser Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic

<400> SEQUENCE: 8

Asp Ile Val Ile Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
```

```
                20                  25                  30
Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105

<210> SEQ ID NO 9
<211> LENGTH: 398
<212> TYPE: DNA
<213> ORGANISM: Artificial Sequence
<220> FEATURE:
<223> OTHER INFORMATION: Synthetic

<400> SEQUENCE: 9
ctgcaggtgt ccactcccag gttcagctgc agcagtctgg agctgagctg atgaagcctg      60
gggcctcagt gaagatatcc tgcaaggcta ctggctacac attcagtagc tactggatag     120
agtgggtaaa gcagaggcct ggacatggcc ttgagtggat tggagagatt ttacctggaa     180
gtggtagtac taactacaat gagaagttca agggcaaggc cacattcact gcagatacat     240
cctccaacac agcctacatg caactcagca gcctgacatc tgaggactct gccgtctatt     300
actgtgcaag agggggggaca gctcgggcta cccactatgc tatggactac tggggtcaag     360
gaacctcagt caccgtctcc tcagagagtc atctggcc                            398

<210> SEQ ID NO 10
<211> LENGTH: 122
<212> TYPE: PRT
<213> ORGANISM: Artificial Sequence
<220> FEATURE:
<223> OTHER INFORMATION: Synthetic

<400> SEQUENCE: 10

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gly Leu Ser Ser Leu Thr Ser Glu Asp Ser Ala Val Tyr Tyr Cys
                85                  90                  95

Ala Arg Gly Gly Thr Ala Arg Ala Thr His Tyr Ala Met Asp Tyr Trp
            100                 105                 110

Gly Gln Gly Thr Ser Val Thr Val Ser Ser
        115                 120

<210> SEQ ID NO 11
<211> LENGTH: 700
<212> TYPE: DNA
<213> ORGANISM: Artificial Sequence
```

<220> FEATURE:
<223> OTHER INFORMATION: Synthetic

<400> SEQUENCE: 11

```
ccgcgggaat tcgatttctg gcggtggcgg atcggatatt gtgataaccc agactcccaa     60
attcctgctt gtatcagcag gagacagggt taccataacc tgcaaggcca gtcagagtgt    120
gagtaatgat gtagcttggt accaacagaa gccagggcag tctcctaaac tgctgatata    180
ctatgcatcc aatcgctaca ctggagtccc tgatcgcttc actggcagtg gatatgggac    240
ggatttcact ttcaccatca gcactgtgca ggctgaagac ctggcagttt atttctgtca    300
gcaggattat agctctccgt acacgttcgg aggggggacc aagctggaaa taaaacgggc    360
tgatgctgca ccaactgtat ccatcttccc accatccagt gagcagttaa catctggagg    420
tgcctcagtc gtgtgcttct gaacaacttc tacccaaa gacatcaatg tcaagtggaa      480
gattgatggc agtgaacgac aaaatggcgt cctgaacagt tggactgatc aggacagcaa    540
agacagcacc tacagcatga gcagcaccct cacgttgacc aaggacgagt atgaacgaca    600
taacagctat acctgtgagg ccactcacaa gacatcaact tcacccattg tcaagagctt    660
caacaggaat gagtgtaatc actagtgaat tcgcggccgc                          700
```

<210> SEQ ID NO 12
<211> LENGTH: 214
<212> TYPE: PRT
<213> ORGANISM: Artificial Sequence
<220> FEATURE:
<223> OTHER INFORMATION: Synthetic

<400> SEQUENCE: 12

```
Asp Ile Val Ile Thr Gln Thr Pro Lys Phe Leu Leu Val Ser Ala Gly
  1               5                  10                  15

Asp Arg Val Thr Ile Thr Cys Lys Ala Ser Gln Ser Val Ser Asn Asp
             20                  25                  30

Val Ala Trp Tyr Gln Gln Lys Pro Gly Gln Ser Pro Lys Leu Leu Ile
         35                  40                  45

Tyr Tyr Ala Ser Asn Arg Tyr Thr Gly Val Pro Asp Arg Phe Thr Gly
     50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Glu Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Phe Ile Val Lys Ser
        195                 200                 205
```

```
Phe Asn Arg Asn Glu Gln
    210
```